United States Patent
Inoue

(10) Patent No.: US 6,287,769 B1
(45) Date of Patent: Sep. 11, 2001

(54) METHOD OF AMPLIFYING DNA FRAGMENT, APPARATUS FOR AMPLIFYING DNA FRAGMENT, METHOD OF ASSAYING MICROORGANISMS, METHOD OF ANALYZING MICROORGANISMS AND METHOD OF ASSAYING CONTAMINANT

(75) Inventor: Takakazu Inoue, Ushiku (JP)

(73) Assignees: Sanyo Electric Co., Ltd., Osaka-fu; Society for Techno-Innovation of Agriculture, Forestry and Fisheries, Tokyo, both of (JP)

( * ) Notice: Subject to any disclaimer, the term of this patent is extended or adjusted under 35 U.S.C. 154(b) by 0 days.

(21) Appl. No.: 09/281,418

(22) Filed: Mar. 30, 1999

(30) Foreign Application Priority Data

Mar. 31, 1998 (JP) .................................................. 10-087651
Mar. 16, 1999 (JP) .................................................. 11-069694

(51) Int. Cl.[7] ............................................................ C12Q 1/68
(52) U.S. Cl. ................................ 435/6; 435/5; 435/91.2; 935/77; 935/78; 935/76; 536/23.1; 536/24.3
(58) Field of Search ........................ 435/6, 91.2; 935/76, 935/77, 78; 536/23.1, 24.3

(56) References Cited

U.S. PATENT DOCUMENTS

| | | |
|---|---|---|
| 4,683,195 | 7/1987 | Mullis et al. . |
| 4,683,202 | 7/1987 | Mullis . |
| 4,965,188 | 10/1990 | Mullis et al. . |
| 5,038,852 | 8/1991 | Johnson et al. . |
| 5,333,675 | 8/1994 | Mullis et al. . |
| 5,670,315 | * 9/1997 | Yamamoto et al. ...................... 435/6 |
| 5,705,332 | * 1/1998 | Roll .......................................... 435/6 |
| 5,753,467 | * 5/1998 | Jensen et al. ....................... 435/91.2 |
| 5,846,783 | * 12/1998 | Wu et al. ............................. 425/91.2 |
| 5,948,615 | * 9/1999 | Uematsu et al. ......................... 435/6 |
| 5,998,136 | * 12/1999 | Kamb ...................................... 435/6 |

FOREIGN PATENT DOCUMENTS

| | | |
|---|---|---|
| 5-192147 | 8/1993 | (JP) . |
| 7-255482 | 10/1995 | (JP) . |

OTHER PUBLICATIONS

Perkin Elmer Catalog, PCR Reagents and Consumables, p. 66, Sep. 1995.*

* cited by examiner

*Primary Examiner*—W. Gary Jones
*Assistant Examiner*—Janell E. Taylor
(74) *Attorney, Agent, or Firm*—Akin, Gump, Strauss, Hauer & Feld, L.L.P.

(57) ABSTRACT

An apparatus for amplifying DNA fragments is formed by a support plate. A plurality of openings are formed on the upper surface of the support plate. A plurality of primers having different amplification probabilities are arranged in the plurality of openings in order of the amplification probabilities. A plurality of microorganisms contained in a microorganism flora are simultaneously amplified with all primers by a random PCR method, for obtaining an electrophoretic pattern amplified at the optimum amplification probability for each microorganism. The plurality of microorganisms contained in the microorganism flora can be discriminated by analyzing the electrophoretic pattern.

22 Claims, 13 Drawing Sheets

F I G. 5
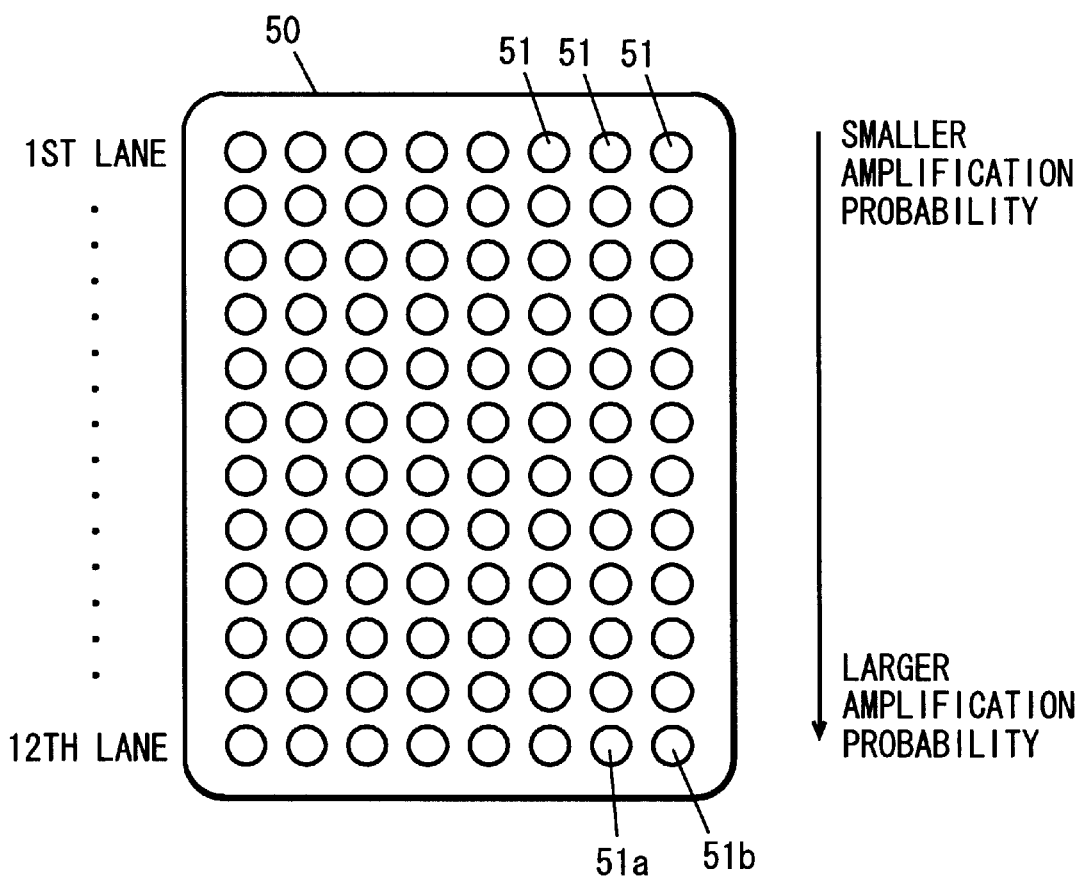

MIXED SAMPLE OF 5 TYPES OF SINGLE ISOLATED BACTERIA

1 : GACCTGCGATCT (SEQUENCE NO. 64)
2 : TGGCCTCTTGGA (SEQUENCE NO. 65)
3 : GGTTTCCCAGGA (SEQUENCE NO. 66)
4 : TCGTTCCGGAGAT (SEQUENCE NO. 67)
5 : CGCTTCGTAGCA (SEQUENCE NO. 68)
6 : GGCTTCGAATCG (SEQUENCE NO. 69)
7 : GATGAGCTAAAA (SEQUENCE NO. 70)
8 : GAGCAGGAATAT (SEQUENCE NO. 71)

HOUSEHOLD GARBAGE DISPOSAL BACTERIAL FLORA

1 : GACCTGCGATCT (SEQUENCE NO. 64)
2 : TGGCCTCTTGGA (SEQUENCE NO. 65)
3 : GGTTTCCCAGGA (SEQUENCE NO. 66)
4 : TCGTCCGGAGAT (SEQUENCE NO. 67)
5 : CGCTTCGTAGCA (SEQUENCE NO. 68)
6 : GGCTTCGAATCG (SEQUENCE NO. 69)
7 : GATGAGCTAAAA (SEQUENCE NO. 70)
8 : GAGCAGGAATAT (SEQUENCE NO. 71)
M : DNA Marker ($\lambda$/Hind III + BioLad AmpliSize Standard)

US 6,287,769 B1

METHOD OF AMPLIFYING DNA FRAGMENT, APPARATUS FOR AMPLIFYING DNA FRAGMENT, METHOD OF ASSAYING MICROORGANISMS, METHOD OF ANALYZING MICROORGANISMS AND METHOD OF ASSAYING CONTAMINANT

BACKGROUND OF THE INVENTION

1. Field of the Invention

The present invention relates to a method of amplifying DNA fragments, an apparatus for amplifying DNA fragments, a method of assaying microorganisms, a method of analyzing microorganisms and a method of assaying a contaminant.

2. Description of the Prior Art

In recent years, a garbage disposal for composting organic waste (the so-called kitchen garbage) discharged from a household kitchen or the like is now actively researched and developed. In the garbage disposal, microorganisms such as bacteria and protozoa degrade organic matter to form compost.

During the composting process (organic degradation process) in such a garbage disposal, the degree of composting is evaluated by monitoring the temperature or the like. The state of the garbage disposal is adjusted to prepare high-quality compost on the basis of the evaluation.

In order to prepare high-quality compost, it is necessary to obtain information of the microorganisms (at least the types of the microorganisms) functioning in the garbage disposal. The information of the microorganisms is also necessary for excellently controlling degradation of the kitchen garbage with the microorganisms. In order to improve soil by adding the prepared compost, it is also important to obtain information of microorganisms contained in the soil.

In general, information of microorganisms such as bacteria, for example, is obtained by a method of isolating each bacterium included in the bacteria and biochemically examining the same. However, this method requires much time, and it is difficult to analyze a bacterium which is hard to isolate by this method.

On the other hand, a PCR (polymerase chain reaction) method is employed for amplifying DNA (U.S. Pat. Nos. 4,683,195, 4,683,202, 4,965,188, 5,038,852 and 5,333,675). In the PCR method, a primer having a base sequence complementary to that at both ends of DNA (template DNA) to be amplified and heat-resistant DNA polymerase are employed for repeating a cycle formed by three stages of a thermal denaturation step, an annealing (heat treatment) step and an extension reaction step thereby enabling amplification of DNA fragments substantially identical to the template DNA. Employing this PCR method, a prescribed fragment in DNA of one of a small amount of bacteria can be amplified to hundred thousand to million times, for example.

In order to employ the PCR method, however, the base sequence of at least at both ends of a part of the template DNA must be known. If the types and base sequences of the microorganisms functioning in the garbage disposal or existing in the soil are unknown, therefore, DNA fragments of the microorganisms cannot be amplified in the conventional PCR method.

In this regard, there has been proposed a RAPD (random amplified polymorphic DNA) method or AP-PCR (arbitrarily primed-polymerase chain reaction) method of simultaneously amplifying many types of DNA fragments from a single type of DNA with a single primer, with no information of the base sequence. According to this method, the annealing temperature for the primer is reduced while the magnesium ion concentration in a reaction solution is increased during PCR, thereby reducing sequence specificity of the primer in bonding. Thus, the primer is bonded to chromosome DNA of a microorganism with mismatching, to duplicate DNA fragments.

According to the RAPD method or AP-PCR method, some DNA fragments are amplified in a large amount with a single primer, with no information on the base sequence of the DNA to be amplified. A DNA fingerprint is obtained by separating the amplified DNA fragments by gel electrophoresis. The state of the microorganism can be elucidated by analyzing the DNA fingerprint.

When applying the conventional RAPD method or AP-PCR method to a group of microorganisms formed by a plurality of microorganisms, however, the number of types of amplified DNA fragments is so large that it is difficult to associate a microorganism which is a template with amplified DNA fragments, and hence it is difficult to discriminate an ecosystem formed by the group of microorganisms.

In order to examine presence/absence of contaminants in soil, food or the like and the degree thereof, the soil or food must be analyzed by suitable methods varying with the types of the contaminants. Particularly when examining the contaminated state of organic matter, it is necessary to predict the types of contaminants for analyzing the same since the analytic methods vary with the elements contained in the organic matter. Thus, awaited is a method of effectively predicting the types of the contaminants.

SUMMARY OF THE INVENTION

An object of the present invention is to provide a method of amplifying DNA fragments capable of correctly discriminating a plurality of different DNA, an apparatus for amplifying DNA fragments, and a highly reliable method of assaying microorganisms and a method of analyzing microorganisms employing the same.

Another object of the present invention is to provide a method of assaying a contaminant capable of readily assaying presence/absence of a contaminant in soil, food or the like and the degree thereof.

A method of amplifying DNA fragments according to an aspect of the present invention comprises steps of preparing a plurality of primers having different amplification probabilities and simultaneously applying a polymerase chain reaction method of repeating a thermal denaturation step, a primer annealing step and an extension reaction step with polymerase in this order to a plurality of different DNA with each of the plurality of primers, thereby amplifying DNA fragments of the plurality of different DNA. The DNA includes not only that of organisms but also DNA fragments.

In the method of amplifying DNA fragments according to this aspect of the present invention, DNA fragments of a plurality of DNA having different base lengths can be amplified by simultaneously applying the polymerase chain reaction method to the plurality of different DNA with each of the plurality of primers having different amplification probabilities. Therefore, a plurality of microorganisms included in a group of microorganisms can be correctly discriminated.

Further, a plurality of types of DNA fragments are obtained from single DNA by employing the plurality of primers having different amplification probabilities. Thus, a plurality of information can be obtained from each microorganism included in the group of microorganisms, for improving the precision of assay.

Preferably, the method further comprises a step of employing a reference primer having a known base sequence and applying the polymerase chain reaction method to reference DNA having a base sequence complementary to that of the reference primer thereby amplifying a DNA fragment of the reference DNA, simultaneously with amplifying the DNA fragments of the plurality of different DNA.

The reference DNA has the base sequence complementary to the reference primer. Therefore, the DNA fragment is reliably amplified from the reference DNA by the polymerase chain reaction method. The amplification efficiency for the DNA fragment of the reference DNA in polymerase chain reaction can be obtained by quantitatively analyzing the amplified DNA fragment of the reference DNA. In this case, the polymerase chain reaction method is simultaneously applied under the same conditions to the reference DNA and the plurality of different DNA, and hence the amplification efficiency obtained from the DNA fragment of the reference DNA is also applicable to the DNA fragments of the plurality of different DNA. Therefore, the quantity of the DNA fragments of the plurality of different DNA can be corrected on the basis of the obtained amplification efficiency.

The method may further comprise a step of classifying the DNA fragments amplified from the plurality of different DNA by a discrimination method. Thus, a plurality of microorganisms included in a group of microorganisms can be correctly discriminated.

Further, the discrimination method may be electrophoresis.

An apparatus for amplifying DNA fragments according to another aspect of the present invention comprises a plurality of reaction solution storage parts and a plurality of primers having different amplification probabilities arranged in the plurality of reaction solution storage parts respectively.

In the apparatus for amplifying DNA fragments according to this aspect of the present invention, the plurality of primers having different amplification probabilities are arranged in the plurality of reaction solution storage parts respectively, whereby DNA fragments of a plurality of DNA can be simultaneously amplified by simultaneously applying the polymerase chain reaction method to the plurality of different DNA with each of the plurality of primers having different amplification probabilities. Thus, a plurality of microorganisms included in a group of microorganisms can be correctly discriminated.

Further, a plurality of types of DNA fragments are obtained from single DNA by simultaneously employing the plurality of primers having different amplification probabilities. Thus, a plurality of information can be obtained from each microorganism included in a group of microorganisms, for improving the precision of assay.

A method of assaying a group of microorganisms according to still another aspect of the present invention comprises steps of preparing a plurality of primers having different amplification probabilities, simultaneously applying a polymerase chain reaction method of repeating a thermal denaturation step, a primer annealing step and an extension reaction step with polymerase in this order to DNA of a plurality of different microorganisms with each of the plurality of primers thereby amplifying DNA fragments of the DNA of the plurality of different microorganisms, and classifying the amplified DNA fragments by a discrimination method for discriminating the plurality of microorganisms included in the group of microorganisms.

In the method of assaying a group of microorganisms according to this aspect of the present invention, DNA fragments can be amplified from the plurality of different microorganisms by simultaneously applying the polymerase chain reaction method to the DNA of the plurality of different microorganisms with each of the plurality of primers having different amplification probabilities. Thus, the plurality of microorganisms included in the group of microorganisms can be correctly discriminated.

Further, a plurality of types of DNA fragments are obtained from a microorganism by employing the plurality of primers having different amplification probabilities. Thus, a plurality of information can be obtained from each microorganism included in the group of microorganisms, for improving the precision of assay. Consequently, various microorganismal ecosystems can be correctly assayed in a short time.

While the number of types of microorganisms forming a group of microorganisms to be assayed and the size of chromosome DNA of the microorganisms are generally unknown, the result of amplification with primers amplifying a proper number of types of DNA fragments can be selected from an electrophoretic pattern by simultaneously employing primers having different amplification probabilities or different orders of amplification probabilities.

By employing a plurality of primers having a proper amplification probability selected in the aforementioned manner, DNA fragments can be amplified from microorganisms even if the number of types of the microorganisms forming the group of target microorganisms is unknown, for examining the number of types of the microorganisms forming the group of microorganisms from the number of types of the amplified DNA fragments.

By employing a plurality of primers having a proper amplification probability selected in the aforementioned manner, further, DNA fragments can be amplified from a principal microorganism or principal group of microorganisms also when the type of the principal group of microorganism forming the group of microorganisms is unknown, for predicting the size of chromosome DNA of the principal microorganism or the principal group of microorganisms from the number of types of the amplified DNA fragments. In addition, it is possible to examine from the predicted size of the chromosome DNA whether microorganisms forming the principal group of microorganisms belong to bacteria, actinomycetes or protozoa.

Preferably, the method further comprises steps of employing a reference primer having a known base sequence and applying the polymerase chain reaction method to reference DNA having a base sequence complementary to that of the reference primer thereby amplifying a DNA fragment of the reference DNA, simultaneously with amplifying DNA fragments of DNA of the plurality of different microorganisms, classifying the DNA fragment amplified from the reference DNA along with the DNA fragments amplified from the DNA of the plurality of different microorganisms by the discrimination method, obtaining the amplification efficiency for the reference DNA on the basis of the result of classification of the DNA fragment amplified from the reference DNA, and correcting the results of classification of the DNA fragments amplified from the plurality of different microorganisms on the basis of the obtained amplification efficiency.

In this case, the DNA fragment is reliably amplified from the reference DNA by the polymerase chain reaction method with the reference primer. The amplification efficiency for the DNA fragment of the reference DNA in the polymerase chain reaction can be obtained from the result of classification of the DNA fragment of the reference DNA thus amplified. The amplification efficiency obtained in this manner is also applicable to the DNA fragments of the DNA of the plurality of different microorganisms. Therefore, the quantity of the DNA fragments can be analyzed by correcting the results of classification of the DNA fragments of the DNA of the plurality of different microorganisms on the basis of the obtained amplification efficiency.

The discrimination method may be electrophoresis. In this case, the amplified DNA fragments are classified by the electrophoresis. Thus, the amplified DNA fragments appear in an electrophoretic pattern as bands classified in response to the size.

Preferably, the method further comprises steps of employing a DNA size marker along with the DNA fragments amplified from the DNA of the plurality of different microorganisms for the electrophoresis, staining an electrophoretic pattern obtained by the electrophoresis, and correcting the gradient of the electrophoretic pattern on the basis of the luminous intensity of a band of the DNA fragment amplified from the reference DNA or the DNA size marker.

In this case, the electrophoretic pattern obtained by the electrophoresis is stained for acquiring a stained electrophoretic image. Influence exerted by the degree of staining or the degree of exposure in image acquisition can be eliminated by correcting the gradient of the electrophoretic pattern on the basis of the luminous intensity of the band of the DNA fragment amplified from the reference DNA or the DNA size marker. Consequently, luminous intensities of bands in the electrophoretic pattern can be correctly compared.

Preferably, the method further comprises steps of setting a threshold based on the luminous intensity of the band of the DNA fragment amplified from the reference DNA or the DNA size marker in the electrophoretic pattern, and analyzing the group of microorganisms on the basis of a band having a luminous intensity exceeding the threshold in the electrophoretic pattern.

In this case, a band having a luminous intensity less than the threshold is that of a DNA fragment having low amplification efficiency and low reproducibility. The band having the luminous intensity exceeding the threshold is that of a DNA fragment having high amplification efficiency and high reproducibility. Thus, only the DNA fragment having high amplification efficiency and high reproducibility can be analyzed by employing the band having the luminous intensity exceeding the threshold. Thus, reliability of information obtained by analysis is improved.

The method may further comprise steps of isolating a bacterium, applying the polymerase chain reaction method to the isolated bacterium with each of the plurality of primers thereby amplifying a DNA fragment of DNA of the bacterium, classifying the DNA fragment amplified from the DNA of the bacterium by the discrimination method, and analyzing the results of discrimination of the DNA fragments amplified from the DNA of the plurality of different microorganisms on the basis of the result of classification of the DNA fragment amplified from the DNA of the bacterium.

Thus, bacteria of the same type as the bacterium isolated from the plurality of different microorganisms can be specified.

A method of analyzing a group of microorganisms according to a further aspect of the present invention comprises steps of preparing a plurality of primers having different amplification probabilities, simultaneously applying a polymerase chain reaction method of repeating a thermal denaturation step, a primer annealing step and an extension reaction step with polymerase in this order to DNA of a plurality of different microorganisms included in a first group of microorganisms with each of the plurality of primers thereby amplifying DNA fragments of the DNA of the plurality of different microorganisms included in the first group of microorganisms, classifying the amplified DNA fragments of the DNA of the plurality of microorganisms included in the first group of microorganisms by a discrimination method, simultaneously applying the polymerase chain reaction method to DNA of a plurality of different microorganisms included in a second group of microorganisms with each of the plurality of primers thereby amplifying DNA fragments of the DNA of the plurality of different microorganisms included in the second group of microorganisms, classifying the amplified DNA fragments of the DNA of the plurality of microorganisms included in the second group of microorganisms by the discrimination method, and comparing the results of classification of the first group of microorganisms with those of the second group of microorganisms.

Thus, the plurality of microorganisms included in the first group and second group of microorganisms can be correctly discriminated, while microorganisms included in both of the first and second groups of microorganisms and those included in the first or second group of microorganisms can be specified.

The discrimination method may be electrophoresis.

A method of analyzing groups of microorganisms according to a further aspect of the present invention comprises steps of sampling a group of microorganisms at a plurality of points of time, simultaneously applying a polymerase chain reaction method of repeating a thermal denaturation step, a primer annealing step and an extension reaction step with polymerase in this order to DNA of a plurality of different microorganisms included in the group of microorganisms with each of a plurality of primers having different amplification probabilities thereby amplifying DNA fragments of the DNA of the plurality of different microorganisms included in the group of microorganisms, classifying the amplified DNA fragments by a discrimination method, and analyzing time change of the states of the group of microorganisms on the basis of the results of classification at the plurality of points of time.

Thus, time change of the number of types of a plurality of microorganisms can be analyzed by analyzing the DNA fragments amplified from the plurality of different microorganisms included in the group microorganisms.

The discrimination method may be electrophoresis.

A method of assaying a contaminant according to a further aspect of the present invention comprises steps of applying a polymerase chain reaction method of repeating a thermal denaturation step, a primer annealing step and an extension reaction step with polymerase in this order to DNA of a microorganism related to a contaminant with each of a plurality of primers having different amplification probabilities thereby amplifying a DNA fragment of the DNA of the microorganism, classifying the DNA fragment amplified from the DNA of the microorganism by a discrimination method, preserving the relation between the type of the microorganism and the result of classification in a database, simultaneously applying the polymerase chain reaction method to DNA of a plurality of different microorganisms contained in an object of assay with each of the plurality of primers thereby amplifying DNA fragments of the DNA of the plurality of different microorganisms, classifying the DNA fragments amplified from the DNA of the plurality of different microorganisms by a discrimination method, and retrieving the types of the plurality of different microorganisms from the database on the basis of the results of classification of the DNA fragments amplified from the plurality of different microorganisms.

In the method of assaying a contaminant according to this aspect of the present invention, the DNA fragment of the DNA of the microorganism related to the contaminant is amplified by the polymerase chain reaction method employing each of the plurality of primers having different amplification probabilities, for classifying this DNA fragment by the discrimination method. The result of classification of the DNA fragment obtained in this manner and the type of the microorganism related to the contaminant are preserved in the database. On the other hand, DNA fragments of the DNA of the plurality of different microorganisms contained in the target are amplified with a plurality of primers similar to the above by the polymerase chain reaction method for classifying the DNA fragments by a classification method similar to the above. The plurality of microorganisms contained in the object of assay can be correctly discriminated by analyzing the results of classification of the DNA fragments of the DNA of the plurality of different microorganisms obtained in this manner. Further, a microorganism related to a contaminant contained in the target can be specified by retrieving the type of the microorganism from the database on the basis of the results of classification. Thus, the contaminant contained in the object of assay can be predicted.

The method may further comprise a step of determining presence/absence of the contaminant in the target on the basis of the result of retrieval of the database.

Thus, the contaminant contained in the object of assay and the contaminated state can be effectively predicted, whereby the contaminant of the object of assay can be assayed by an analytical method suitable for the predicted contaminant.

The database preferably preserves data of a plurality of types of microorganisms and results of classification corresponding thereto.

Thus, a plurality of types of microorganisms related to the contaminant can be specified in the object of assay. Thus, a plurality of contaminants contained in the object of assay can be simultaneously assayed.

The discrimination method may be electrophoresis, and the results of classification may be band patterns of an electrophoretic pattern, and the database may preserve the relation between the types of the microorganisms and the band patterns of the electrophoretic pattern.

Thus, the types of the microorganisms can be retrieved from the band patterns of the electrophoretic pattern.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 5 is a model diagram showing another exemplary apparatus for amplifying DNA fragments employed for the method of amplifying DNA fragments and the method of assaying a group of microorganisms according to the present invention;

DESCRIPTION OF THE PREFERRED EMBODIMENTS

A method of amplifying DNA fragments, an apparatus for amplifying DNA fragments and a method of assaying a group of microorganisms according to an embodiment of the present invention are now described.

Figure 4:
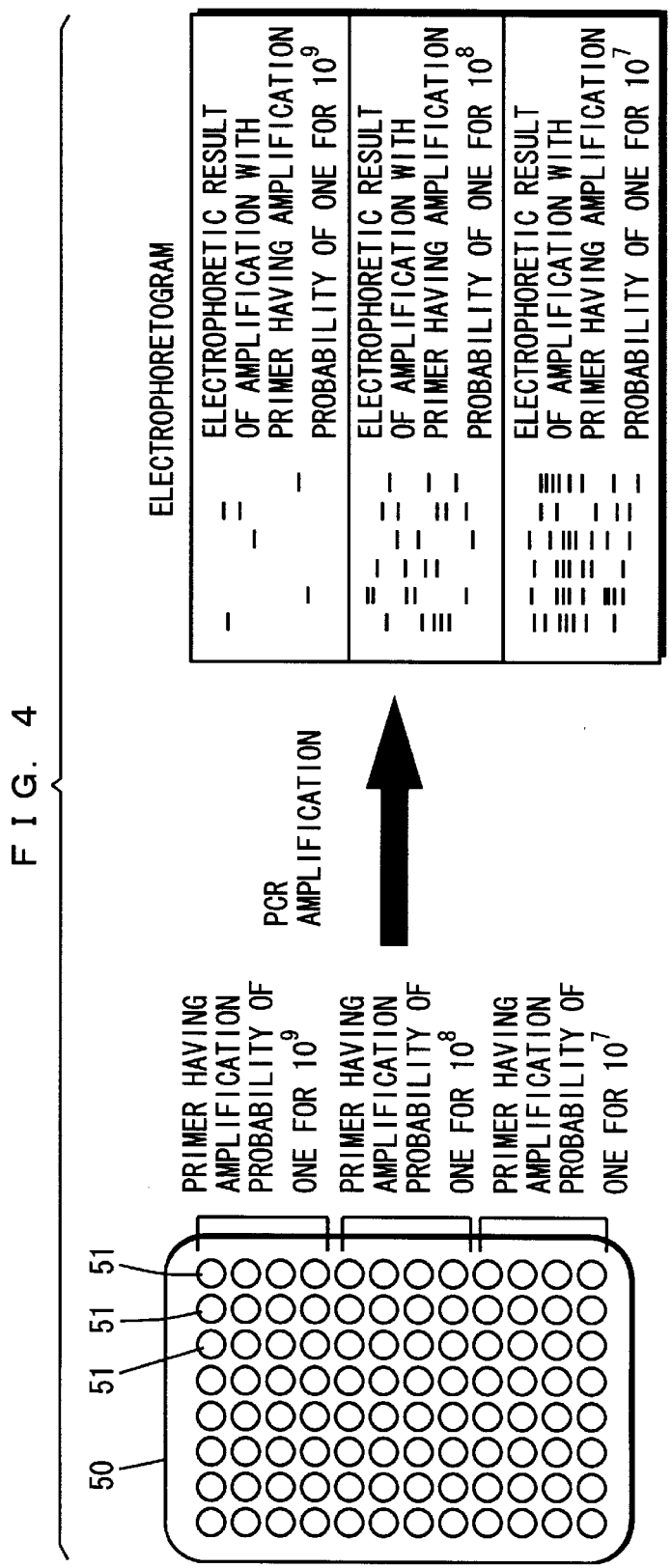
FIG. 4 is a model diagram showing an exemplary apparatus for amplifying DNA fragments employed for a method of amplifying DNA fragments and a method of assaying a group of microorganisms according to the present invention.

FIG. 4 is a model diagram showing an exemplary apparatus for amplifying DNA fragments employed for the method of amplifying DNA fragments and the method of assaying a group of microorganisms according to the present invention.

Referring to FIG. 4, the apparatus for amplifying DNA fragments is formed by a support plate 50 called a titer plate. A plurality of openings (reaction solution storage parts) 51 are formed on the upper surface of the support plate 50. In the example shown in FIG. 4, 96 openings 51 are formed on the upper surface of the support plate 50.

Primers having an amplification probability for amplifying a DNA fragment for $10^9$ bp (base pairs) are arranged in 32 openings 51 closer to an end of the support plate 50. Primers having an amplification probability for amplifying a DNA fragment for $10^8$ bp are arranged in 32 openings 51 at the center of the support plate 50. Primers having an amplification probability for amplifying a DNA fragment for $10^7$ bp are arranged in 32 openings 51 closer to another end of the support plate 50.

FIG. 5 is a model diagram showing another exemplary apparatus for amplifying DNA fragments employed for the method of amplifying DNA fragments and the method of assaying microorganisms according to the present invention.

Also in the apparatus for amplifying DNA fragments shown in FIG. 5, a plurality of openings 51 are formed on the upper surface of a support plate 50. A plurality of primers having different amplification probabilities are continuously arranged in the plurality of openings 51 in order of the amplification probabilities.

Consider that the base length of chromosome DNA of a microorganism is about $10^7$ bp. When setting the amplification probability to amplify a DNA fragment for $10^8$ bp in order to assay a microorganism flora containing 10 types of microorganisms, for example, a DNA fragment is amplified, i.e., a single type of microorganism is detected for 10 types of microorganisms. Therefore, 10 types of microorganisms can be detected by preparing 10 types of primers. In practice, however, 20 to 30 types of primers are preferably prepared in order to cope with unbalanced amplification.

If the microorganism flora contains a number of microorganisms or chromosome DNA of the microorganisms has a large base length, it is effective to set the amplification probability at a low value. If the microorganism flora contains a small number of microorganisms or the chromosome DNA of the microorganisms has a small base length, on the contrary, it is effective to set the amplification probability at a high value.

In the apparatus for amplifying DNA fragments shown in FIG. 4, primers having different amplification probabilities or different orders of amplification probabilities are arranged in order, while 32 types of primers are prepared for each amplification probability. In the apparatus for amplifying DNA fragments shown in FIG. 5, on the other hand, types of primers having different amplification probabilities are prepared in order of the amplification probabilities.

In the apparatus for amplifying DNA fragments shown in FIG. 5, 94 types of primers having different amplification probabilities are arranged in the openings 51 in order of the amplification probabilities while a negative control is arranged in an opening 51a and a positive control is arranged in an opening 51b, for example.

The positive control is a sample employed for a control experiment for eliminating errors caused in a series of steps of amplifying DNA fragments. In general, the amplification efficiency in amplification of DNA fragments is conceivably influenced by errors caused in a series of steps such as errors in concentrations of DNA polymerase, magnesium and the like in preparation of a reaction solution for random PCR, errors in the degree of activation of an employed reagent and the temperature in DNA fragment amplification and the like, for example. In order to eliminate such errors, a reaction solution containing a primer and template DNA for amplifying a known type of DNA fragment quantitatively is prepared as the positive control. The DNA fragment amplified by the positive control can be quantitatively analyzed by electrophoresis. Therefore, the amplification efficiency for the DNA fragment can be obtained from the quantity of the DNA fragment amplified in the positive control. The influence exerted by the errors caused in the series of steps of amplification of DNA fragments can be eliminated by correcting the quantity of DNA fragments in the 94 types of reaction solutions for random PCR on the basis of the amplification efficiency obtained in the aforementioned manner. Consequently, the amplified DNA fragments can be compared in quantity.

On the other hand, the negative control is a sample employed in a control experiment for confirming that amplified DNA fragments belong to an object group of microorganisms or a microorganism to be analyzed. In general, microorganisms such as bacteria exist in various places in the air or the like. In preparation of the reaction solutions for random PCR, therefore, the reaction solutions may be contaminated by microorganisms. In this case, it is impossible to determine whether the amplified DNA fragments are derived from the object microorganisms or the contaminating microorganisms. Therefore, a reaction solution for random PCR containing a primer with no template DNA is prepared as the negative control. Random PCR and electrophoresis are performed with the negative control, to confirm that no band appears on the electrophoretic pattern of the negative control. Thus, it is possible to confirm that the amplified DNA fragments are derived from the object group of microorganisms or the object microorganism to be analyzed.

Each of the primers employed for the positive control and the negative control may have the same base sequence as one or two of the 94 types of primers.

A plurality of microorganisms contained in the microorganism flora are simultaneously amplified with all primers by a random PCR (polymerase chain reaction) method described later. The random PCR method is a reaction method of chain-reactionally amplifying DNA fragments from a plurality of different microorganisms having unknown base sequences with primers having a specific base sequence.

As shown in FIG. 4, a number of bands appear in the electrophoretic pattern of the DNA fragments amplified with the primers having a high amplification probability. On the contrary, a small number of bands appear in the electrophoretic pattern of the DNA fragments amplified with the primers having a low amplification probability. Thus, microorganisms can be analyzed on the basis of an electrophoretic pattern amplified at the optimum amplification probability in response to the number of types of microorganisms contained in the object microorganism flora, the size of chromosomes of the microorganisms, the number of types of DNA fragments or the size of the DNA fragments.

The random PCR method employed for the method of amplifying DNA fragments and the method of assaying a group of microorganisms according to the present invention is now described.

In the random PCR method employed in the method of amplifying DNA fragments according to the present invention, the following three stages of steps are repeated similarly to the conventional PCR method. In this random PCR method, primers having a specific base sequence are employed for a plurality of different microorganisms having unknown base sequences thereby amplifying an analyzable quantity of DNA fragments, as described later.

(1) Thermal Denaturation Step DNA (initial state) or a DNA fragment is heated and denatured into single strands (DNA strands).

(2) Primer Annealing Step (Primer Bonding Step) Heat treatment is performed to bond a primer to an end of an amplification region of each DNA strand.

(3) Extension Reaction Step with Polymerase (Duplication Step with Polymerase)

Starting from the primer, a complementary strand is synthesized by polymerase to form a double strand.

A cycle formed by the above steps (1) to (3) is repeated.

The random PCR method is now described more specifically. First prepared is a reaction solution containing a plurality of different microorganisms, a buffer solution for polymerase chain reaction, primers, heat-resistant thermophile DNA polymerase and four types of 5'-deoxyribonucleotide triphosphates (dATP, dGTP, dCTP and dTTP) serving as substrates.

The DNA polymerase is an enzyme having substrates of four types of 5'-deoxyribonucleotide triphosphates for catalyzing polymerization reaction of DNA strands having a base sequence complementary to template DNA. The directionality of polymerization of DNA strands with the DNA polymerase is at the 5' to 3' ends. The primers are DNA fragments (short oligonucleotides) having 3'-OH groups essential for the action of the DNA polymerase on ends thereof. In the present invention, primers having a specific base sequence and a specific base length are employed.

The following random PCR method is applied to the above reaction solution:

As a first cycle, a thermal denaturation step of keeping the above reaction solution at 94° C. for two minutes, for example, a primer annealing step of keeping the above reaction solution at 45° C. for two minutes, for example, and an extension reaction step with polymerase for keeping the above reaction solution at 72° C. for three minutes, for example, are carried out in this order. The time for the thermal denaturation step in this cycle is set longer than those in second and third cycles, in order to completely separate long complete DNA into single strands.

Then, as the second cycle, a thermal denaturation step of keeping the above reaction solution at 94° C. for one minute, for example, a primer annealing step of keeping the above reaction solution at 45° C. for two minutes, for example, and an extension reaction step with polymerase for keeping the above reaction solution at 72° C. for three minutes, for example, are repeated in this order 33 times, for example.

Finally, as the third cycle, a thermal denaturation step of keeping the above reaction solution at 94° C. for one minute, for example, a primer annealing step of keeping the above reaction solution at 45° C. for two minutes, for example, and an extension reaction step with polymerase for keeping the above reaction solution at 72° C. for 10 minutes, for example, are carried out in this order. In this cycle, the time for the extension reaction step with polymerase is set longer than those in the first and second cycles, in order to finally complete duplication.

Figure 1:
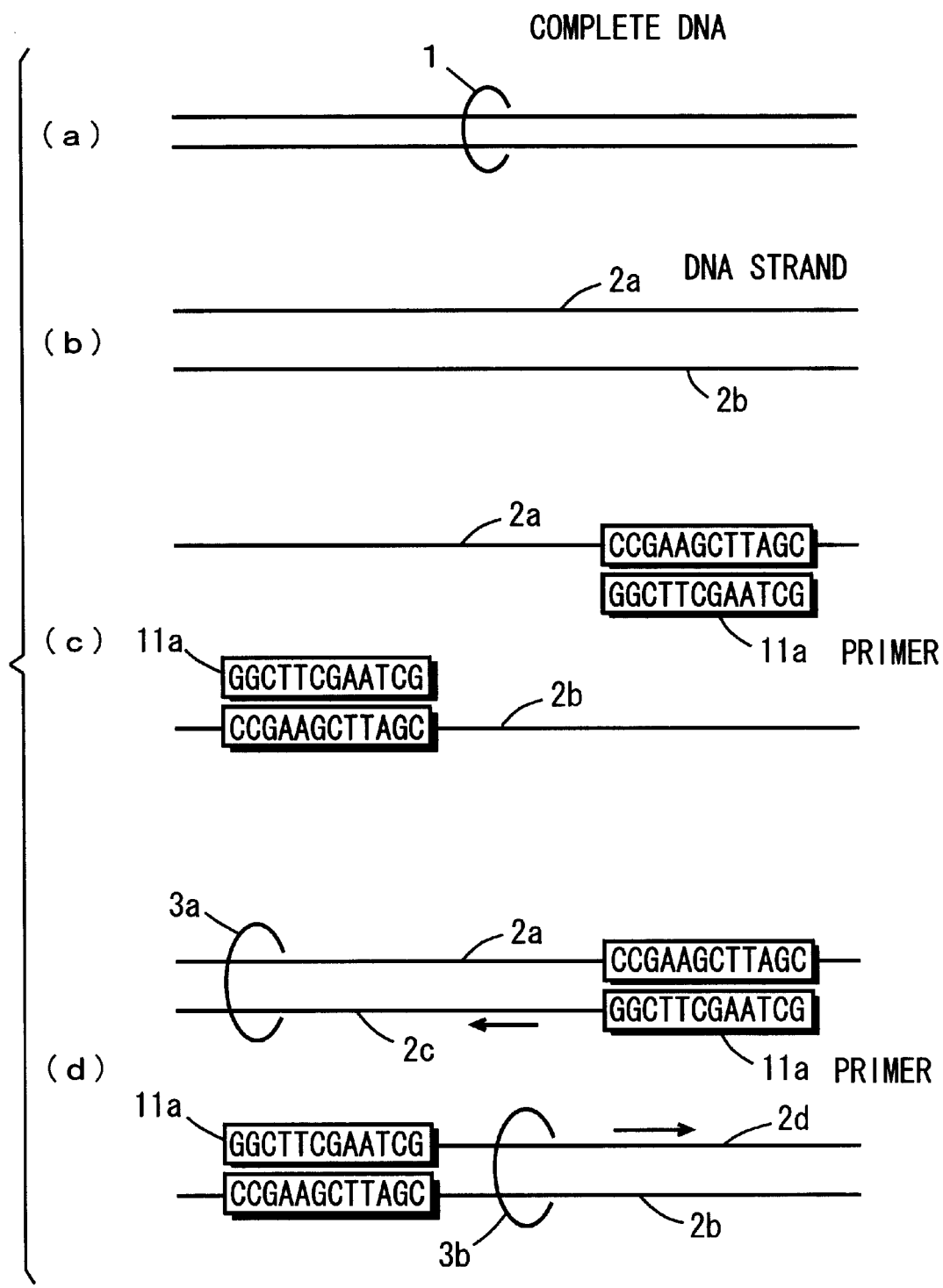
FIG. 1 is a model diagram showing the process in a first cycle in a random PCR method.
Figure 2:
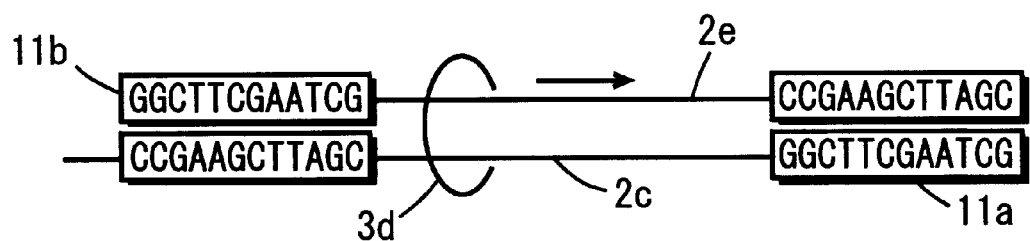
FIG. 2 is a model diagram showing the process in a first time of a second cycle in the random PCR method.
Figure 3:
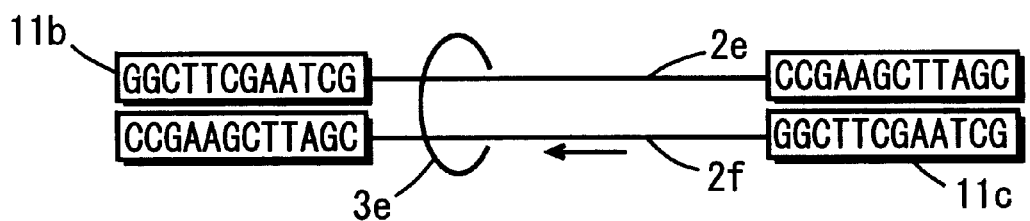
FIG. 3 is a model diagram showing the process in a second time of the second cycle in the random PCR method.

The first cycle, a first time of the second cycle and a second time of the second cycle are now described with reference to FIGS. 1 to 3. FIGS. 1 to 3 are model diagrams showing single strands of DNA etc. with the base sequence of parts bonded to the primers.

Referring to FIGS. 1 to 3, the primers have a base sequence (sequence No. 69) of GGCTTCGAATCG. T stands for thymine, A for adenine, G for guanine, and C for cytosine.

As shown at (a) in FIG. 1, long DNA (complete DNA) 1 contained in a plurality of different microorganisms initially exists in the above reaction solution. The following description is made with reference to single complete DNA 1.

First, the thermal denaturation step longer than those in the second and third cycles is carried out in the first cycle, so that the long DNA 1 is heated, denatured and separated into two single strands (DNA strands) 2a and 2b from a double-stranded state, as shown at (b) in FIG. 1.

Then, in the primer annealing step, each primer 11a is bonded to be arranged (complementarily arranged) on a compatible position of each of the single strands 2a and 2b compatible with its base sequence, as shown at (c) in FIG. 1. The term compatible position stands for the position of the base sequence to be bonded as viewed from that of the primer or the position of a base sequence similar to that to be bonded as viewed from the base sequence of the primer. In the aforementioned random PCR method, the annealing temperature for the primer annealing step is set at a low value so that the primer is bonded also to a part of the DNA strand having a base sequence similar to its base sequence. In other words, the primer can be bonded not only to the position of the single strand having the base sequence completely complementary to its base sequence but also to the single strand with slight mismatching. Referring to FIGS. 1 to 3, each primer is bonded to the position of the base sequence to be bonded as viewed from its base sequence, for simplifying the illustration.

Then, in the extension reaction step with polymerase, extension reaction is caused by the polymerase so that single strands 2c and 2d extend along the single strands 2a and 2b respectively to form double strands 3a and 3b, as shown at (d) in FIG. 1.

In the first time of the second cycle, the strands 3a and 3b doubled in the first cycle are separated into the single strands (DNA strands) 2a and 2c and the single strands (DNA strands) 2b and 2d respectively through the thermal denaturation step, while the following description is made with reference to the single strand 2c separated from the strand 3a.

As shown in FIG. 2, a primer 11b is bonded to the single strand 2c separated through the thermal denaturation step to be arranged on a compatible position in the subsequent primer annealing step. Thereafter in the extension reaction step with polymerase, extension reaction is caused by the polymerase so that a single strand 2e extends along the single strand 2c to form a double strand 3d.

Thereafter the double strand 3d is separated into the single strands 2c and 2e through the thermal denaturation step in the second time of the second cycle as shown in FIG. 3, while the following description is made with reference to the single strand 2e separated from the strand 3d.

As shown in FIG. 3, a primer 11c is bonded to the single strand 2e separated through the thermal denaturation step to be arranged on a compatible position in the subsequent primer annealing step. Thereafter in the extension reaction step with polymerase, extension reaction is caused by the polymerase so that a single strand 2f extends along the single strand 2e to form a double strand (DNA fragment) 3e.

The DNA fragment is thus formed so that another DNA fragment is formed from this DNA fragment while DNA fragments are formed from another DNA of the same type followed by chain-reactional continuation of similar reaction, whereby DNA fragments are amplified by this method.

Gel electrophoresis is applied to the DNA fragments amplified by the aforementioned random PCR method, in order to classify the same in response to the different microorganisms. The existential states of the microorganisms can be estimated by analyzing bands on the electrophoretic pattern. Alternatively, the aforementioned random PCR method is applied to microorganisms sampled at time intervals for amplifying DNA fragments and gel electrophoresis is similarly applied to the amplified DNA fragments. Time change of the existential states of the microorganisms can be estimated by analyzing state change of bands on the electrophoretic pattern.

When a primer is strongly bonded to and arranged on a compatible position of template DNA having a prescribed base sequence in amplification of DNA fragments by the random PCR method, amplification efficiency for the DNA fragments is high. The DNA fragments amplified with such a primer appear as clear bands having high reproducibility on an electrophoretic pattern. When bonding between the primer and the compatible position of the template DNA is weak, on the other hand, the primer is bonded to another position having stronger bonding than the compatible position of the template DNA. Thus, the amplification reaction of DNA fragments so competitively progresses that the amplification efficiency for the DNA fragments is reduced if the bonding between the primer and the template DNA is weak. DNA fragments amplified with such a primer having weak bonding appear as unclear bands having low reproducibility on the electrophoretic pattern. When containing such DNA fragments having low reproducibility, data obtained by the random PCR method are inferior in total reliability.

Figure 6:
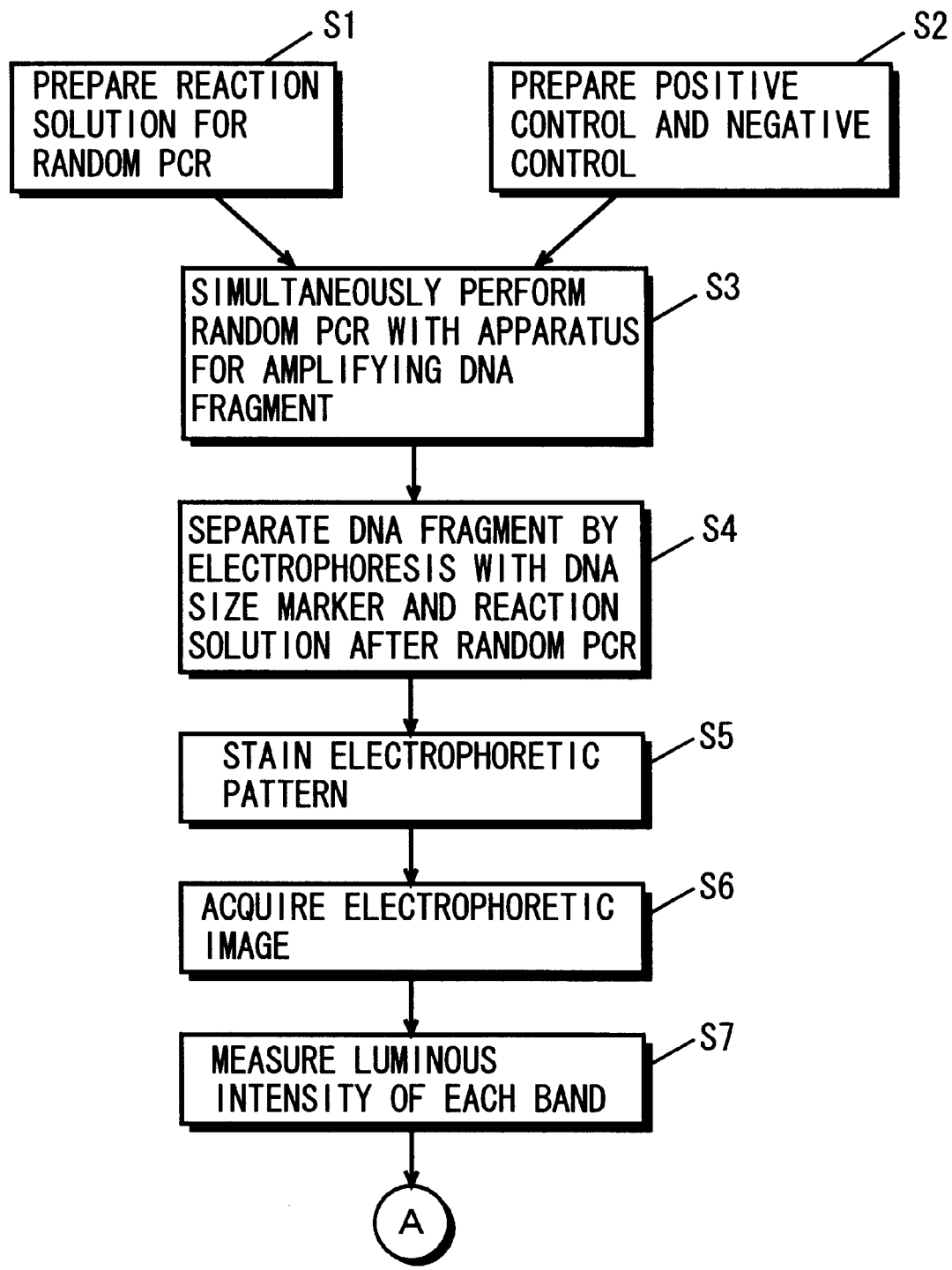
FIG. 6 is a flow chart showing an exemplary image processing method employed for the method of assaying a group of microorganisms according to the present invention.
Figure 7:
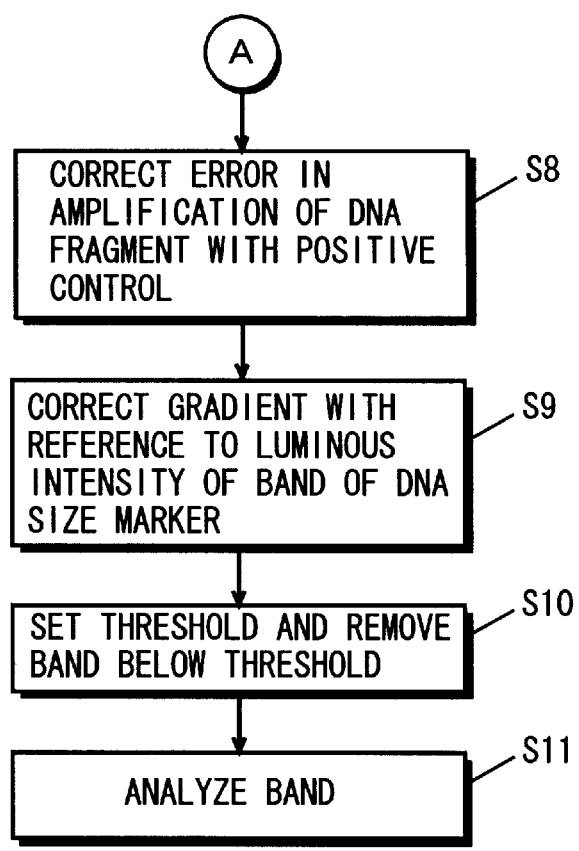
FIG. 7 is a flow chart showing an exemplary image processing method employed for the method of assaying a group of microorganisms according to the present invention.

In order to improve the reliability of data obtained by the random PCR method, the following image processing is performed in the method of assaying a group of microorganisms according to the present invention:

FIG. 6 and FIG. 7 are flow charts showing an example of the method of assaying a group of microorganisms according to the present invention.

As shown in FIG. 6 and FIG. 7, prescribed quantities of a buffer solution, $MgCl_2$, bases (A, T, G and C), primers, DNA and DNA polymerase are mixed with each other to prepare a reaction solution for random PCR (step S1). In the random PCR employing a plurality of primers having different amplification probabilities, the reaction solution for random PCR is prepared for each primer. When employing 94 types of primers, for example, 94 types of reaction solutions for random PCR containing different primers are prepared. All of the 94 types of reaction solutions for random PCR are prepared at the same time.

Simultaneously with preparation of the reaction solutions for random PCR, a positive control and a negative control are prepared (step S2). The details of the positive control and the negative control are described above with reference to the apparatus for amplifying DNA fragments.

Then, DNA fragments are amplified by the random PCR method with the apparatus for amplifying DNA fragments (step S3). Thereafter the DNA fragments amplified in each reaction solution are fractioned per size by electrophoresis with the reaction solutions for random PCR, the positive control and the negative control and at the same time the DNA size marker having a known concentration and quantity is also fractioned (step S4). Further, electrophoretic patterns obtained through the electrophoresis are stained with a fluorochrome (step S5), for acquiring fluorescent images irradiated with ultraviolet light (step S6). Further, the electrophoretic images are incorporated in a computer with a scanner, and subjected to data processing for measuring the size and the luminous intensities of each band (step S7). If no band appears in the electrophoretic pattern of the negative control, it is possible to confirm that the amplified DNA fragments are derived from an object of a group of microorganisms.

Then, the amplified DNA fragment of the positive control is quantitatively analyzed by comparing the luminous intensity of the band of the positive control with that of the DNA size marker having a known quantity, for obtaining the amplification efficiency in the DNA fragment amplification reaction (step S8). Alternatively, the positive control may be quantitatively analyzed by another method of measuring absorption of ultraviolet light at 260 nm after purifying the DNA fragment, for example.

Further, the luminous intensities of the bands of the reaction solutions for random PCR are corrected with reference to the luminous intensity of the band of the quantitatively analyzable DNA size marker. Thus, the gradients of the electrophoretic images are corrected (step S9).

In general, errors are caused in the gradients of the electrophoretic images depending on the degrees of staining with ethidium bromide and the degrees of exposure in the image. Such errors can be eliminated by correcting the gradients of the electrophoretic images on the basis of the luminous intensity of the band of the DNA size marker having a known concentration.

Then, a threshold is set on the basis of the luminous intensity of the band of the quantitatively analyzable DNA size marker obtained by measurement, for removing bands having luminous intensities less than the threshold (step S10). Thus, bands having low amplification efficiency and low reproducibility can be removed. Bands having high amplification efficiency and high reproducibility thus obtained are analyzed for obtaining reliable data of the microorganisms.

In the random PCR method, a plurality of types of primers are employed for amplifying DNA fragments from chromosome DNA of one of bacteria at prescribed amplification probabilities, and hence the number of types of bacteria is correlated with that of the amplified DNA fragments such that the total number of the amplified DNA fragments reflects the number of types of bacteria. Thus, the number of types of a plurality of microorganisms included in the group of microorganisms can be examined by analyzing the DNA fragments. As to DNA fragments amplified by the same primer, bands appear on the same positions of electrophoretic patterns. Thus, the same type of microorganisms can be discriminated between a microorganism flora and isolated microorganisms or between microorganism florae by analyzing the bands appearing on the same positions.

When applying the aforementioned method of assaying a group of microorganisms to microorganisms sampled at time intervals, change of existential states of the microorganisms can be estimated from change of the total number of amplified DNA fragments.

Figure 8:
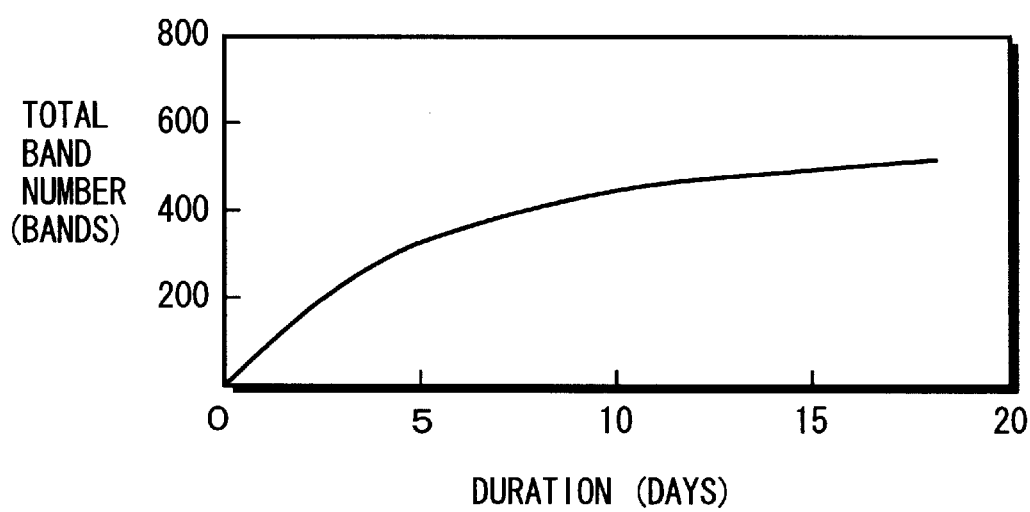
FIG. 8 illustrates time change of DNA fragments amplified from a group of microorganisms inhabiting in the tank of a garbage disposal.

When applying the aforementioned method of assaying a group of microorganisms to microorganisms sampled from the tank of a garbage disposal at time intervals, for example, the total number of bands appearing in electrophoretic patterns changes as shown in FIG. 8.

In the tank containing wood chips as a treating carrier, only a small amount of microorganisms exist and hence the total band number is small in the initial state, as shown in FIG. 8. However, the total band number increases as the days go on. The total band number increases since the tank is contaminated by a plurality of types of bacteria existing in kitchen garbage daily introduced into the tank, while the number of bacteria increases since those slow in multiplication multiply with time. Assuming that the mean band number of a single type of bacterium is 20, it is estimable that 20 types of bacteria exist on the fifth day since the band number of the fifth day is 400.

When applying the aforementioned method of amplifying DNA fragments to a plurality of microorganisms sampled from the tank of a garbage disposal or soil, existential states of the microorganisms contained in the tank of the garbage disposal or the soil can be estimated. When examining the existential states of microorganisms similarly sampled from the tank of the garbage disposal or the soil at time intervals, time change of the existential states of microorganisms in the tank of the garbage disposal or the soil can be estimated. In a degradation process of organic matter contained in kitchen garbage, further, the degraded state of the organic matter can also be estimated.

When changing the conditions of the tank of the garbage disposal in accordance with the results of the estimation, kitchen garbage can be excellently treated while preparing excellent compost.

Alternatively, a microorganism isolated from a group of microorganisms is identified by biochemical examination while analyzing the band pattern of DNA of the identified microorganism by the aforementioned method of assaying a group of microorganisms. Thus, the types of a plurality of microorganisms and band patterns of DNA thereof may be analyzed for establishing a database of the band patterns of the DNA of the microorganisms on the basis of the obtained data. In this case, DNA of microorganisms sampled from the tank of the garbage disposal or soil is analyzed by the aforementioned method of assaying a group of microorganisms and the types of the microorganisms are retrieved from the database on the basis of obtained band patterns of the DNA of the microorganisms. Thus, the types of the microorganisms forming the group of microorganisms can be examined. In particular, the method of retrieving the types of microorganisms from the aforementioned database is effective to find out soil, food or the like contaminated by toxic contaminants such as mercury, arsenic, dioxin, environmental hormones and the like and recognize the contaminated state. The database is searched on the basis of the band patterns of the DNA of the microorganisms for identifying the types of the microorganisms forming the object group of microorganisms. When the identified microorganisms include those related to the contaminants, such a possibility is suggested that the contaminants are contained in the soil from which the microorganisms have been sampled. Further, the existential degree of the microorganisms related to the contaminants suggests the contaminated state of the soil. Tables 1 and 2 show exemplary contaminants and microorganisms related thereto.

TABLE 1

| Classification | Substance Name | Related Microorganism |
|---|---|---|
| Agricultural chemicals | organic phosphorus such as parathion | *Pseudomonas diminuta* |
| | carbamate | *Achromobacter* sp. |
| | triazine | *Rhodococcus* sp. *Rhodococcus corallinus. Phanerochaete chrysosporium* |
| | organic chlorine | *Alcaligenes eutrophus Flavobacterium* sp. *Pseudomonas cepacia* |
| Insecticide | γ-BHC | *Pseudomonas paucimobilis Sphingomonas paucimobilis* |
| | PCP | *Rhodococcus chlorophenolicus Pseudomonas* sp. *Phanerochaete chrysosporium Phanerochaete sordida* |
| Plastic | polyvinyl alcohol | *Pseudomonas putida Pseudomonas vesicularis* |

TABLE 1-continued

| Classification | Substance Name | Related Microorganism |
|---|---|---|
| | polyether (polyethylene glycol) | *Pseudomonas aeruginosa Bacteroides* sp. *Pelolobacter venetianus Rhizobium loti Corynebacterium* sp. *Sphingomonas pegritica* |
| | polyester polyurethane polyamide | *Penicillium* sp. *Rhizobium delemar Corynebacterium aurantiacum Flavobacterium* sp. |

TABLE 2

| Classification | Substance Name | Related Microorganism |
|---|---|---|
| Metal | mercury | *Pseudomonas* sp. *Methanobacterium omelianskii Clostridium cochearium* |
| | chromium | *Streptococcus lactis Alcaligenes eutrophus Pseudomonas aeruginosa Enterobacter cloacae* |
| | cadmium | *Staphlococcus aureus Alcaligenes eutrophus* |
| | aluminum | *Chaetosphaeria inaequalis Paecilomyces lilacinus Metarhizium anisopliae Penicillium glabrum Aspergillus fumigatus Sporothrix inflata Emericellopsis minima* |
| | iron | *Thiobacillus ferrooxidans Thiobacillus thiooxidans Leptospirillum ferooxidans* |
| | arsenic | *Alcaligenes faecalis Pseudomonas* sp. *Micrococcus lactilyticus Staphylococcus aureus* |
| Chlorine Organic Compound | chlorobenzoic acid | *Pseudomonas putida Alcaligenes eutrophus* |
| | chlorobenzene etc. | *Alcaligenes eutrophus* |
| | dioxin | *Phanerochaete chrysosporium* |

If the soil contains Methanobacterium, Clostridium or Pseudomonas bacteria as shown in Tables 1 and 2, for example, the possibility of soil contamination with mercury is suggested. Further, it is also possible to estimate presence/absence of dioxin and the existential degree thereof from Phanerochaete which can degrade dioxin.

According to the aforementioned method of retrieving microorganisms from the database of band patterns of DNA, the types of contaminants and the degrees thereof can be quickly examined by collecting a small quantity of sample of soil or food allowing no prediction of the contaminants.

EXAMPLES

Example 1

High-quality primers employed for the method of amplifying DNA fragments according to the present invention were selected in the following method:

① Primers and Standard Samples 216 types of DNA oligomers by Nippon Gene were employed as primers to be studied. Further, chromosome DNA samples of seven bacteria shown in Table 3 were employed as standard samples for selecting the primers.

TABLE 3

Seven Types of Bacteria employed for Primer Selection

1. *Escherichia coli* strain K12
2. *Bacillus subtilis* natto strain I2
3. No. 10 (bacterium isolated from garbage disposal)
4. No. 30 (bacterium isolated from garbage disposal)
5. No. 38 (bacterium isolated from garbage disposal)
6. No. 46 (bacterium isolated from garbage disposal)
7. No. 103 *Proteus mirabilis* (bacterium isolated from garbage disposal)

As shown in Table 3, *Escherichia coli* strain K12 and *Bacillus subtilis* natto strain I2 were employed as representatives of general bacteria. Further, bacteria degrading kitchen garbage in the tank of a garbage disposal were employed as the remaining five bacteria. Nos. 10, 30, 38, 46 and 103 are allotted to the five bacteria respectively.

② Method of Driving Garbage Disposal

Household garbage disposal SNS-T1 (outer dimensions: 580 by 450 by 795 mm) by Sanyo Electric Co., Ltd. was employed and improved by connecting an air pump and an air adjuster to an outlet of this garbage disposal. The garbage disposal was set in a prefabricated laboratory of 30° C. in temperature and 60% in relative humidity.

Wood chips (Japan cedar material of 1.5 mm in mean particle diameter) of 25 kg (water content: 70%) were introduced into the tank of the garbage disposal as a treating carrier. 1 kg of kitchen garbage consisting of 450 g of vegetables, 300 g of fruit, 40 g of fish, 30 g of meat and 180 g of cooked rice was introduced into the garbage disposal five times a week (once a day), and thereafter the contents of the tank were stirred with stirring blades of the garbage disposal.

The water content of the wood chips was adjusted to 35 to 45% in the tank, for keeping an excellent treating state. The water content was finely controlled by adjusting the volume of air introduced from the air pump with the air adjuster.

③ Isolation of Bacteria for Treating Kitchen Garbage

An agar medium for culturing bacteria was prepared in the composition shown in Table 4.

TABLE 4

| nutrient broth medium (Eiken E-MC35) | 18 g/L |
| --- | --- |
| sodium chloride | 0.5M |
| pH | adjusted to 9 with sodium hydroxide |
| agar | 15 g/L |

After a lapse of about nine months from starting driving the garbage disposal, 10 g of the wood chips were sampled from the tank and suspended until bacteria were sufficiently isolated from the wood chips with addition of 90 mL of a sterilized 0.85% salt solution. The suspension was diluted to $10^{-6}$, and 100 μL of the diluted suspension was homogeneously inoculated on the agar medium. After cultivation at 37° C. for three days, all colonies were transferred to a new agar medium for isolating the bacteria.

Among the isolated colonies, five types of bacteria having different colony shapes were employed as standard samples for PCR. The above Nos. 10, 30, 38, 46 and 103 were allotted to the isolated bacteria. As the result of biochemical examination, it has been recognized that the bacterium No. 103 is *Proteus mirabilis*.

④ Method of Preparing Chromosome DNA of Bacteria employed as Standard Samples

*Escherichia coli* strain K12 and *Bacillus subtilis* natto strain I2 were cultured on a nutrient broth medium (Eiken E-MC35) of 18 g/L for 16 hours. The five bacteria isolated from the garbage disposal were cultured on a medium shown in Table 5 for 16 hours.

TABLE 5

| nutrient broth medium (Eiken E-MC35) | 18 g/L |
| --- | --- |
| sodium chloride | 0.5M |
| pH | adjusted to 9 with sodium hydroxide |

The chromosome DNA samples of the bacteria were prepared in accordance with the method of "Preparation of Genomic DNA from Bacteria" described in Current Protocols in Molecular Biology (published by Greene Publishing Associates and Wiley-Interscience), pp. 2.4.1 to 2.4.2.

⑤ Setting of PCR Conditions

In the random PCR method employed in the present invention, it is difficult to associate each of a plurality of microorganisms with DNA fragments if a number of DNA fragments are amplified from a single type of microorganism. Therefore, the number of amplified DNA fragments must be reduced by increasing selectivity of amplification. Important factors for improving the selectivity are the length of the primers, the magnesium concentration in the reaction solution composition, the annealing temperature in the reaction cycle and the number of the reaction cycle.

The PCR conditions were set through PCR System 9700 by PE Applied Biosystem and DNA amplifier MIR-D40 by Sanyo Electric Co., Ltd.

The PCR conditions were studied with DNA Oligomer H81 by Nippon Gene employed as a primer having a base length of 12 bp. In this study, the reaction solution was composed of Tris-HCl of 10 mMin concentration, KCl of 50 mMin concentration and each of dATP, dCTP, dGTP and dTTP of 200 μM in concentration. Consequently, it has been recognized that the optimum values of the magnesium concentration and the Taq polymerase concentration are 1.5 mM and 0.025 unit/μL respectively and the optimum values of the annealing temperature for the PCR cycle and the cycle number are 55° C. and 35 cycles respectively. The efficiency of PCR reaction slightly changes due to influence by the type of the primer and set conditions. In consideration of this, the annealing temperature was set at 45° C. in the following primer selection experiment, in order to slightly reduce the selectivity.

Table 6 shows the composition of the reaction solution employed for random PCR in the following primer selection experiment.

TABLE 6

| | Final Concentration |
| --- | --- |
| buffer | |
| Tris-HCl (pH 8.3) | 10 mM |
| KCl | 50 mM |
| MgCl$_2$ | 1.5 mM |
| dNTPmix | 200 μM |
| primer | 2 μM |

TABLE 6-continued

| | Final Concentration |
|---|---|
| chromosome DNA | 10 pg/μL |
| Taq DNA polymerase | 0.025 u/μL |

Referring to Table 6, Tris in Tris-HCl is the abbreviation of Tris(hydroxymethyl)aminomethane. dNTPmix stands for an isosbestic mixed solution of dATP (2'-deoxyadenosine-5'-triphosphate), dCTP (2'-deoxycytidine-5'-triphosphate), dGTP (2'-deoxyguanosine-5'-triphosphate) and dTTP (2'-deoxythymidine-5'-triphosphate). The quantity of the reaction solution was 20 μm.

Table 7 shows cycles of random PCR in the primer selection experiment.

TABLE 7

| | |
|---|---|
| 94° C. for 1 min. | 1 cycle |
| 94° C. for 1 min. + 45° C. for 2 min. + 72° C. for 3 min. | 35 cycles |
| 72° C. for 7 min. | 1 cycle |
| 4° C. (end of reaction, preserved) | |

⑥ Primer Selection Experiment

Seven types of random PCR experiments were made for each primer employing the aforementioned seven bacteria as standard samples, and 5 μL of the reaction solution was analyzed by 1.5% agarose gel electrophoresis after random PCR. The electrophoresis was made under a constant voltage of 3.6 V/cm. After the electrophoresis, the gel was stained with ethidium bromide and irradiated with ultraviolet light of 254 nm in wavelength for acquiring ethidium bromide fluorescent images with an instant camera.

⑦ Selection of Primers

The numbers of bands observed from the electrophoretic images were counted. Tables 8 to 15 show the band numbers (total band numbers) observed from 216 types of primers (sequence Nos. 1 to 216) and the electrophoretic images.

TABLE 8

| No. | | Base Sequence 5' → 3' | GC % | Total Band Number |
|---|---|---|---|---|
| 1 | A26 | ACTGAGAAAATA | 25.0 | 0 |
| 2 | A49 | ATCTTCAAAGAT | 25.0 | 0 |
| 3 | A64 | ACAAAGAGATAT | 25.0 | 0 |
| 4 | A47 | GAGGTGATATTA | 33.3 | 0 |
| 5 | A66 | ATCTTCTCATCT | 33.3 | 0 |
| 6 | A71 | ACTCTTCTACAA | 33.3 | 0 |
| 7 | A88 | AGAGACATAGTT | 33.3 | 0 |
| 8 | B08 | GCCAGATATATA | 33.3 | 0 |
| 9 | B24 | CACACTACTTAT | 33.3 | 0 |
| 10 | B26 | ATGAGAAAGGAA | 33.3 | 0 |
| 11 | B45 | ATCAACACTTTC | 33.3 | 0 |
| 12 | B64 | GAGACTACAATA | 33.3 | 0 |
| 13 | B91 | CCATACATATTG | 33.3 | 0 |
| 14 | C12 | GATACTGATGAT | 33.3 | 0 |
| 15 | C25 | AGATTCTTACTG | 33.3 | 0 |
| 16 | D01 | AGCCCTTATTTA | 33.3 | 0 |
| 17 | D05 | GAGACTATGAAA | 33.3 | 0 |
| 18 | D29 | ATCAAGTATCCA | 33.3 | 0 |
| 19 | A23 | ACTGACCTAGTT | 41.7 | 0 |
| 20 | A28 | ATTTGGATAGGG | 41.7 | 0 |
| 21 | A61 | GACTGCTATACA | 41.7 | 0 |
| 22 | A69 | TGGTACGGTATA | 41.7 | 0 |
| 23 | A85 | TACTACTGTGGA | 41.7 | 0 |
| 24 | B84 | TGGCTGTAGAAA | 41.7 | 0 |
| 25 | C32 | TCTACACGAAGT | 41.7 | 0 |
| 26 | C42 | CCAGATTTTCTG | 41.7 | 0 |

TABLE 8-continued

| No. | | Base Sequence 5' → 3' | GC % | Total Band Number |
|---|---|---|---|---|
| 27 | C51 | ATCAACGTACGT | 41.7 | 0 |
| 28 | C71 | TTCCGTAATCAC | 41.7 | 0 |
| 29 | C89 | GCTTACATAGAC | 41.7 | 0 |
| 30 | D03 | ACTCCAAATGTG | 41.7 | 0 |

TABLE 9

| No. | | Base Sequence 5' → 3' | GC % | Total Band Number |
|---|---|---|---|---|
| 31 | A87 | AAGTCGTTTGGG | 50.0 | 0 |
| 32 | B82 | CTAGTATGGGAC | 50.0 | 0 |
| 33 | C26 | GAGTTCGAACGA | 50.0 | 0 |
| 34 | C61 | ACTTTCCTACGG | 50.0 | 0 |
| 35 | H91 | TTCCCGTCTATC | 50.0 | 0 |
| 36 | C03 | AGCCTTACGGCA | 58.3 | 0 |
| 37 | C67 | GCTATGGCAACG | 58.3 | 0 |
| 38 | C69 | CCTTGGAACTCG | 58.3 | 0 |
| 39 | C31 | TCTGCTGACCGG | 66.7 | 0 |
| 40 | C50 | GGCAACTGGCCA | 66.7 | 0 |
| 41 | B28 | GTCATTAAAGCT | 33.3 | 1 |
| 42 | D10 | TACACTTTTGAC | 33.3 | 1 |
| 43 | B88 | TGGATCTTTGAC | 41.7 | 1 |
| 44 | C06 | GCTCTTTTGGAA | 41.7 | 1 |
| 45 | C49 | ATCATCGTACGT | 41.7 | 1 |
| 46 | C68 | TACGATATGGCT | 41.7 | 1 |
| 47 | C87 | GATCCAGTCTTT | 41.7 | 1 |
| 48 | D27 | AGAATGTCCGTA | 41.7 | 1 |
| 49 | A09 | CCGCAGTTAGAT | 50.0 | 1 |
| 50 | B03 | CAGTGGGAGTTT | 50.0 | 1 |
| 51 | B62 | TCTATGGACCCT | 50.0 | 1 |
| 52 | C11 | TTCATTCTGGGG | 50.0 | 1 |
| 53 | C23 | CCGTCTTTTCTG | 50.0 | 1 |
| 54 | A82 | TGGCCTATTGGC | 58.3 | 1 |
| 55 | B02 | GTCATGCCTGGA | 58.3 | 1 |
| 56 | B92 | CCTTGGCGAAGC | 66.7 | 1 |
| 57 | C41 | AGCCTGTGGGCT | 66.7 | 1 |
| 58 | A21 | AGAATTGGACGA | 41.7 | 2 |
| 59 | A52 | CTTGTCATGTGT | 41.7 | 2 |
| 60 | B63 | TACGTGGTAACA | 41.7 | 2 |

TABLE 10

| No. | | Base Sequence 5' → 3' | GC % | Total Band Number |
|---|---|---|---|---|
| 61 | C45 | GGACAAGTAATG | 41.7 | 2 |
| 62 | A48 | TACCCTCAAGCT | 50.0 | 2 |
| 63 | B52 | TTCGAGGATCGA | 50.0 | 2 |
| 64 | A30 | GACCTGCGATCT | 58.3 | 2 |
| 65 | A81 | TGGCCTCTTGGA | 58.3 | 2 |
| 66 | A83 | GGTTTCCCAGGA | 58.3 | 2 |
| 67 | B06 | TCGTCCGGAGAT | 58.3 | 2 |
| 68 | C05 | CGCTTCGTAGCA | 58.3 | 2 |
| 69 | H81 | GGCTTCGAATCG | 58.3 | 2 |
| 70 | D26 | GATGAGCTAAAA | 33.3 | 3 |
| 71 | A70 | GAGCAGGAATAT | 41.7 | 3 |
| 72 | B30 | CTTAGGTTACGT | 41.7 | 3 |
| 73 | D04 | GTGGATCTGAAT | 41.7 | 3 |
| 74 | A63 | CCTATCCCAACA | 50.0 | 3 |
| 75 | D30 | GAGACTACCGAA | 50.0 | 3 |
| 76 | C66 | GACAGCGTCCTA | 58.3 | 3 |
| 77 | B09 | CTTGAGCGTATT | 41.7 | 4 |
| 78 | B10 | ACTGAGATAGCA | 41.7 | 4 |
| 79 | B42 | GAGAGACGATTA | 41.7 | 4 |
| 80 | A89 | GACGCCCATTAT | 50.0 | 4 |
| 81 | B66 | GACGGTTCTACA | 50.0 | 4 |
| 82 | C46 | GATGGTCCGTTT | 50.0 | 4 |
| 83 | H83 | TTCACCAACGAG | 50.0 | 4 |
| 84 | B07 | CAGGTGTGGGTT | 58.3 | 4 |
| 85 | A86 | ATTGGTGCAGAA | 41.7 | 5 |

TABLE 10-continued

| No. | | Base Sequence 5' → 3' | GC % | Total Band Number |
|---|---|---|---|---|
| 86 | A90 | AAGGCGTGTTTA | 41.7 | 5 |
| 87 | C30 | TATTGGGATTGG | 41.7 | 5 |
| 88 | A92 | AACATCTCCGGG | 58.3 | 5 |
| 89 | B01 | ATCATTGGCGAA | 41.7 | 6 |
| 90 | B69 | TTGAGTAGTTGC | 41.7 | 6 |

TABLE 11

| No. | | Base Sequence 5' → 3' | GC % | Total Band Number |
|---|---|---|---|---|
| 91 | A91 | TACGCCGGAATA | 50.0 | 6 |
| 92 | A67 | CCTGAGGTAGCT | 58.3 | 6 |
| 93 | C47 | GCCGCTTCAGCT | 66.7 | 6 |
| 94 | B90 | ATCTAAACCACG | 41.7 | 7 |
| 95 | C65 | AGAGCTGAAGTA | 41.7 | 7 |
| 96 | A46 | GGTGAGGATTCA | 50.0 | 7 |
| 97 | C07 | CTCAAGCGTACA | 50.0 | 7 |
| 98 | A50 | CCTTTCCGACGT | 58.3 | 7 |
| 99 | H82 | TCCTTCGAGCAG | 58.3 | 7 |
| 100 | B83 | CAGGCCGAAGTC | 66.7 | 7 |
| 101 | B21 | AAGCCTATACCA | 41.7 | 8 |
| 102 | B86 | CGACGATATGAT | 41.7 | 8 |
| 103 | D08 | GCCCTTTTGGAC | 58.3 | 8 |
| 104 | B12 | ACTTTCGATCCA | 41.7 | 9 |
| 105 | B25 | AGCACTGAATCT | 41.7 | 9 |
| 106 | B29 | GCCATCGAAAAA | 41.7 | 9 |
| 107 | H87 | GAGTACACGAAG | 50.0 | 9 |
| 108 | C72 | CTTGAGGGATGG | 58.3 | 9 |
| 109 | A22 | GCCTGCCTCACG | 75.0 | 9 |
| 110 | C81 | AGAGGTGTAAAT | 33.3 | 10 |
| 111 | H84 | AAGCTGCAGCAA | 50.0 | 10 |
| 112 | C09 | GCCTTCGTTACG | 58.3 | 10 |
| 113 | C62 | AGGGCTCTAGGC | 66.7 | 10 |
| 114 | C82 | TTGCATAATCGT | 33.3 | 11 |
| 115 | C08 | GGCAGATATCAT | 41.7 | 11 |
| 116 | A42 | TCCAAGCTACCA | 50.0 | 11 |
| 117 | B72 | TAACAACCGAGC | 50.0 | 11 |
| 118 | B31 | CACAAGGAACAT | 41.7 | 12 |
| 119 | B05 | TCGGTGGGAATA | 50.0 | 12 |
| 120 | H86 | ATGGAGCAGGAA | 50.0 | 12 |

TABLE 12

| No. | | Base Sequence 5' → 3' | GC % | Total Band Number |
|---|---|---|---|---|
| 121 | A29 | GGTTCGGGAATG | 58.3 | 12 |
| 122 | C64 | GAGCTCCCGACA | 66.7 | 12 |
| 123 | B89 | ACTAACCTGGAC | 50.0 | 13 |
| 124 | B11 | GGCGTGGTTGTA | 58.3 | 13 |
| 125 | B41 | GGCGAGGGAGGA | 75.0 | 13 |
| 126 | B47 | GCCGCCAGAGGA | 75.0 | 13 |
| 127 | B71 | TGACACACTGTC | 50.0 | 14 |
| 128 | A01 | TGCACTACAACA | 41.7 | 15 |
| 129 | H85 | CACTTCAACCAG | 50.0 | 15 |
| 130 | B87 | TATCCACCGCTC | 58.3 | 15 |
| 131 | D22 | TGCCCACTACGG | 66.7 | 15 |
| 132 | B44 | GAGACTGCTGAT | 50.0 | 16 |
| 133 | B04 | CAGGTGGGACCA | 66.7 | 16 |
| 134 | B46 | TCCTGGGGCGTT | 66.7 | 16 |
| 135 | B51 | GGCAAGGGATAT | 50.0 | 17 |
| 136 | C27 | GCATTGCAATCG | 50.0 | 17 |
| 137 | D25 | GTTTTGTCACCG | 50.0 | 17 |
| 138 | C70 | GGATCCGACGGC | 75.0 | 17 |
| 139 | C01 | ATGACTGTGCGA | 50.0 | 18 |
| 140 | B48 | GCGTCGGTTCGA | 66.7 | 19 |
| 141 | A24 | CTCCTGCTGTTG | 58.3 | 20 |
| 142 | D28 | ACTGAGGGGGA | 66.7 | 20 |
| 143 | A72 | AAGGACACAACA | 41.7 | 21 |
| 144 | B85 | ACGGGTCGTAAC | 58.3 | 21 |

TABLE 12-continued

| No. | | Base Sequence 5' → 3' | GC % | Total Band Number |
|---|---|---|---|---|
| 145 | H92 | GTCGGACGTCCA | 66.7 | 21 |
| 146 | B50 | ACTGAGCAACAA | 41.7 | 23 |
| 147 | D09 | CACACTCGTCAT | 50.0 | 24 |
| 148 | C29 | GTCGCCTTACCA | 58.3 | 25 |
| 149 | A27 | ATCGCGGAATAT | 41.7 | 26 |
| 150 | B61 | AGACCTGCTTCT | 50.0 | 26 |

TABLE 13

| No. | | Base Sequence 5' → 3' | GC % | Total Band Number |
|---|---|---|---|---|
| 151 | A32 | TTGCCGGGACCA | 66.7 | 26 |
| 152 | B27 | GGCGGTTATGAA | 50.0 | 27 |
| 153 | A41 | GTGACCGATCCA | 58.3 | 27 |
| 154 | C63 | GCTGGCGTATCT | 58.3 | 27 |
| 155 | D12 | GGACCTCCATCG | 66.7 | 27 |
| 156 | H90 | CCGAGGGCTGTA | 66.7 | 27 |
| 157 | A62 | CCTGCGGGAGGA | 75.0 | 27 |
| 158 | A43 | AAGTGGTGGTAT | 41.7 | 28 |
| 159 | B70 | TATCCTACCGGC | 58.3 | 28 |
| 160 | C92 | AGGCACCCTTCG | 66.7 | 28 |
| 161 | C52 | GTCGACGGACGT | 66.7 | 29 |
| 162 | C04 | GAGGAGAAACGG | 58.3 | 30 |
| 163 | H88 | GCTGGATTCGCA | 58.3 | 30 |
| 164 | C22 | GGTCACCGATCC | 66.7 | 30 |
| 165 | B32 | ATCGCGGCTTAT | 50.0 | 31 |
| 166 | D23 | ACCATCAAACGG | 50.0 | 33 |
| 167 | B81 | GGCCGACTTGGC | 75.0 | 33 |
| 168 | C91 | GAGTGGCAACGT | 58.3 | 34 |
| 169 | A84 | CCGCAGGGACCA | 75.0 | 34 |
| 170 | B68 | GGTCAGGAACAA | 50.0 | 35 |
| 171 | B49 | GTCGGTCGTGAA | 58.3 | 35 |
| 172 | D24 | GTGCAATTTGGC | 50.0 | 36 |
| 173 | C10 | ACTCACCACGCA | 58.3 | 36 |
| 174 | C88 | TGGCTTCATCAC | 50.0 | 37 |
| 175 | D06 | CCGTGGAATGAC | 58.3 | 39 |
| 176 | C48 | GGAGGATGGCCC | 75.0 | 39 |
| 177 | C24 | CCTTGGCATCGG | 66.7 | 40 |
| 178 | C86 | GTTAGCCCCAAT | 50.0 | 41 |
| 179 | A02 | GGCATGGCCTTT | 58.3 | 43 |
| 180 | H89 | GGTGACGATGCA | 58.3 | 43 |

TABLE 14

| No. | | Base Sequence 5' → 3' | GC % | Total Band Number |
|---|---|---|---|---|
| 181 | B43 | ACTGGCCGGCAT | 66.7 | 43 |
| 182 | D32 | AAGCTGGGGGGA | 66.7 | 43 |
| 183 | C85 | ATGGCTACTGGC | 58.3 | 44 |
| 184 | B23 | GGTGCCGGAGCA | 75.0 | 44 |
| 185 | A25 | CTCAGCGATACG | 58.3 | 45 |
| 186 | A51 | GGTGGTGGTATC | 58.3 | 45 |
| 187 | C28 | GTCGACGCATCA | 58.3 | 46 |
| 188 | A44 | GACGGTTCAAGC | 58.3 | 47 |
| 189 | C90 | AAGCTGTGGGCT | 58.3 | 48 |
| 190 | A68 | GCGGAGGAACCA | 66.7 | 50 |
| 191 | D02 | CCAGGAGGTGGT | 66.7 | 51 |
| 192 | A65 | AGCGCGGCAAAA | 58.3 | 52 |
| 193 | D07 | ACCACTCCCGCA | 66.7 | 52 |
| 194 | C43 | GGCGGCACAGGA | 75.0 | 52 |
| 195 | A08 | GCCCCGTTAGCA | 66.7 | 53 |
| 196 | A31 | AAGGCGCGAACG | 66.7 | 53 |
| 197 | B22 | GGTGACTGGTGG | 66.7 | 53 |
| 198 | C44 | CGCAGCCGAGAT | 66.7 | 53 |
| 199 | C02 | AAGAAGCAGGCG | 58.3 | 54 |
| 200 | B65 | GTGTGAAGCCA | 58.3 | 58 |
| 201 | A11 | GATGGATTTGGG | 50.0 | 60 |
| 202 | A45 | GGTCAGGCACCA | 66.7 | 63 |
| 203 | A07 | TGCCTCGCACCA | 66.7 | 65 |
| 204 | A05 | AGCAGCGCCTCA | 66.7 | 69 |

TABLE 14-continued

| No. | | Base Sequence 5' → 3' | GC % | Total Band Number |
|---|---|---|---|---|
| 205 | A06 | GCCAGCTGTACG | 66.7 | 72 |
| 206 | D31 | GGAGGTCGACCA | 66.7 | 72 |
| 207 | A12 | TTCGGACGAATA | 41.7 | 74 |
| 208 | C21 | GGAGAGCGGACG | 75.0 | 77 |
| 209 | D21 | GGCGATTCTGCA | 58.3 | 83 |
| 210 | C84 | GTGGGTGGACAA | 58.3 | 87 |

TABLE 15

| No. | | Base Sequence 5' → 3' | GC % | Total Band Number |
|---|---|---|---|---|
| 211 | C83 | GTGCACGTATGG | 58.3 | 89 |
| 212 | A03 | CGACGACGACGA | 66.7 | 89 |
| 213 | A10 | ACTGGCCGAGGG | 75.0 | 89 |
| 214 | B67 | GCGGTCAGCACA | 66.7 | 99 |
| 215 | A04 | ATCAGCGCACCA | 58.3 | 112 |
| 216 | D11 | ATGGCCGGTGGG | 75.0 | 117 |

Figure 9:
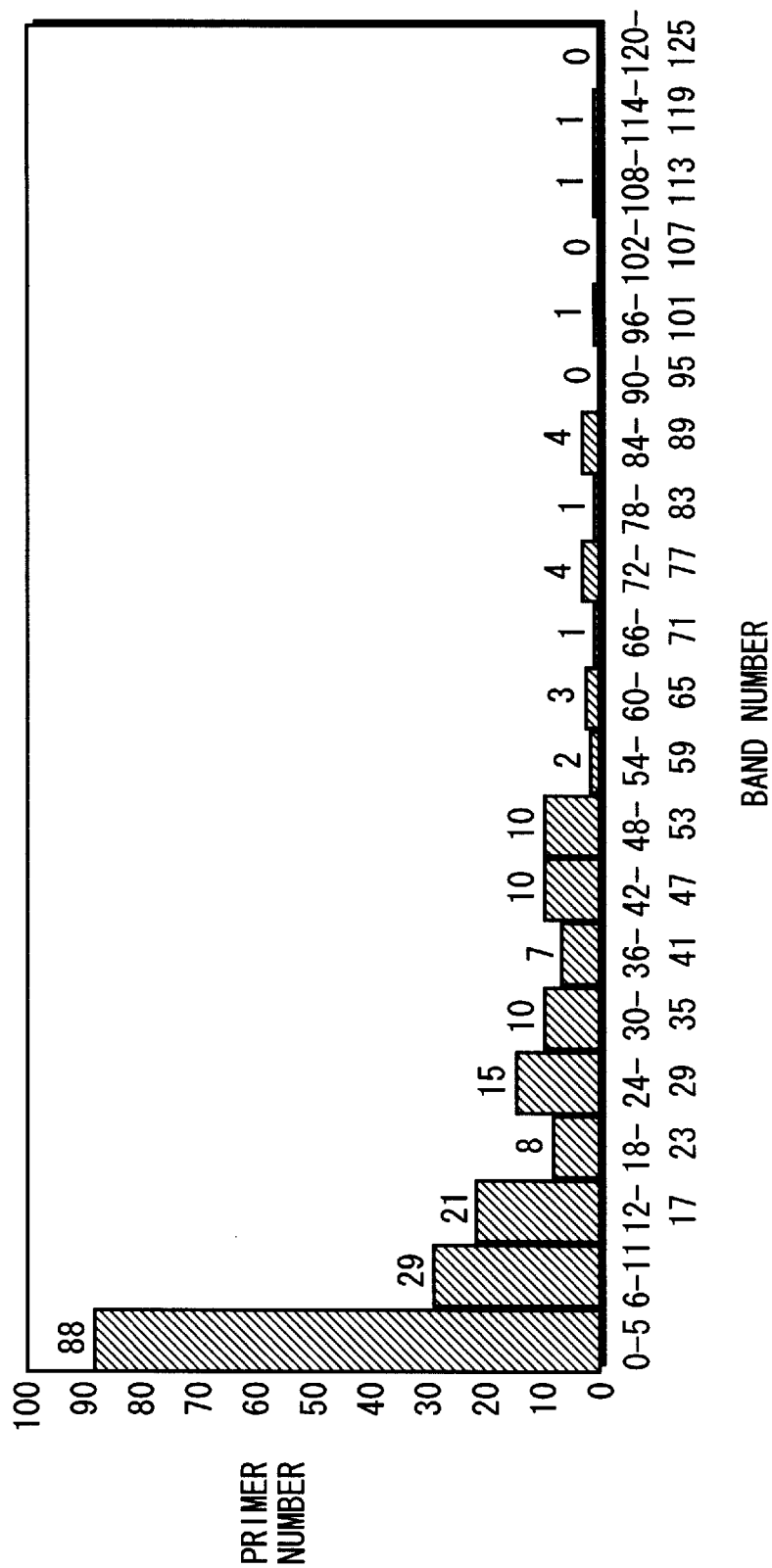
FIG. 9 illustrates the distribution of primer numbers every six bands.

The band numbers, varying with the primers, were distributed in the range of 0 to 117. FIG. 9 shows the primer numbers every six bands. Most of the primers were shifted to smaller band numbers.

Figure 10:
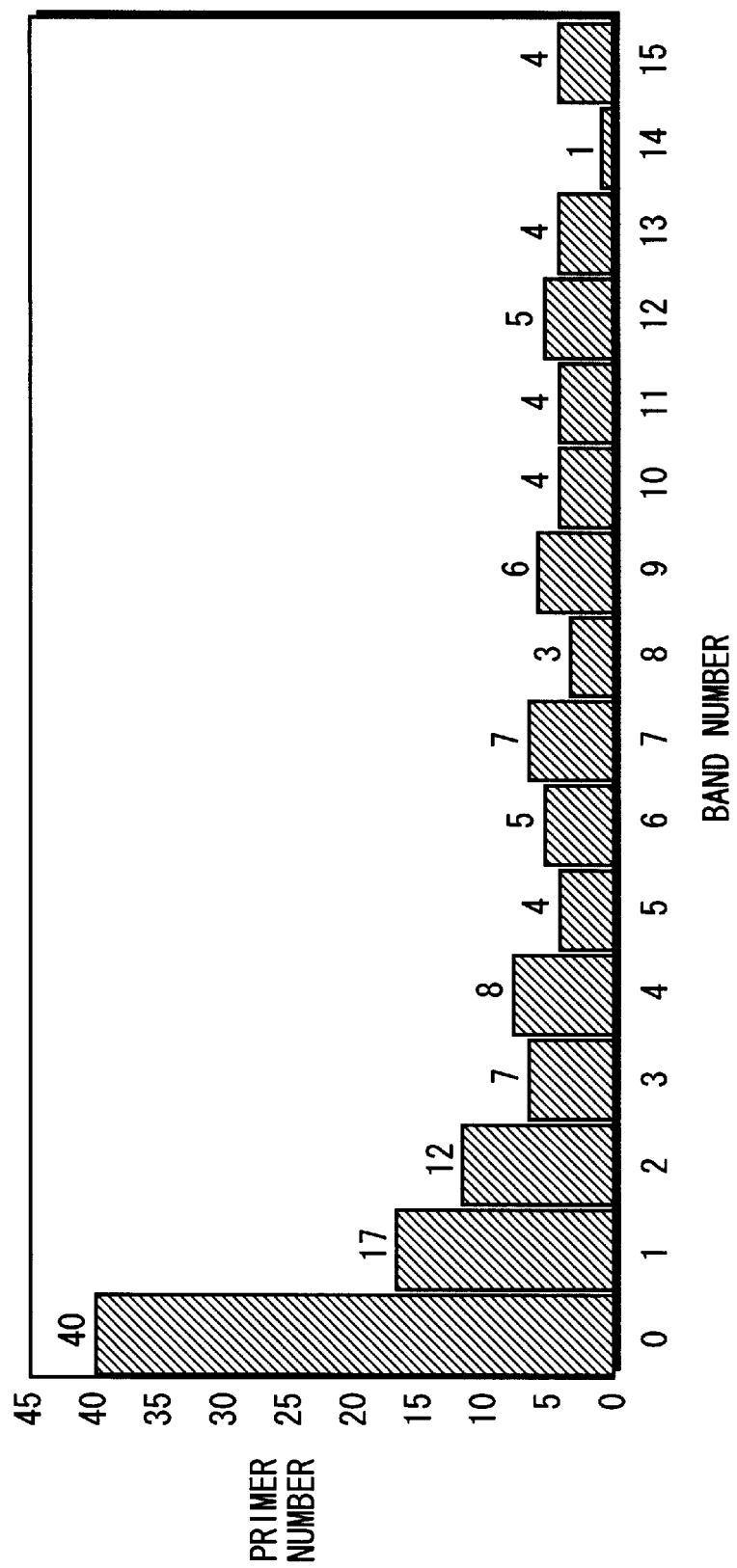
FIG. 10 illustrates the numbers of primers for the respective band numbers as to primers each having not more than 15 bands.

The inventive method of amplifying DNA fragments requires primers having the minimum appearance frequencies of bands in the electrophoretic patterns. FIG. 10 illustrates the numbers of primers for the respective band numbers as to primers each having not more than 15 bands.

Although the primers have the same length of 12 bp (base pairs), the appearance frequencies of the bands remarkably vary with the types of the primers, due to difference in affinity between the primers and template DNA. One of the indications deciding the affinity is the GC content. The GC content stands for the ratio occupied by the total number of C and G for the total number of the four bases A, C, G and T.

Figure 11:
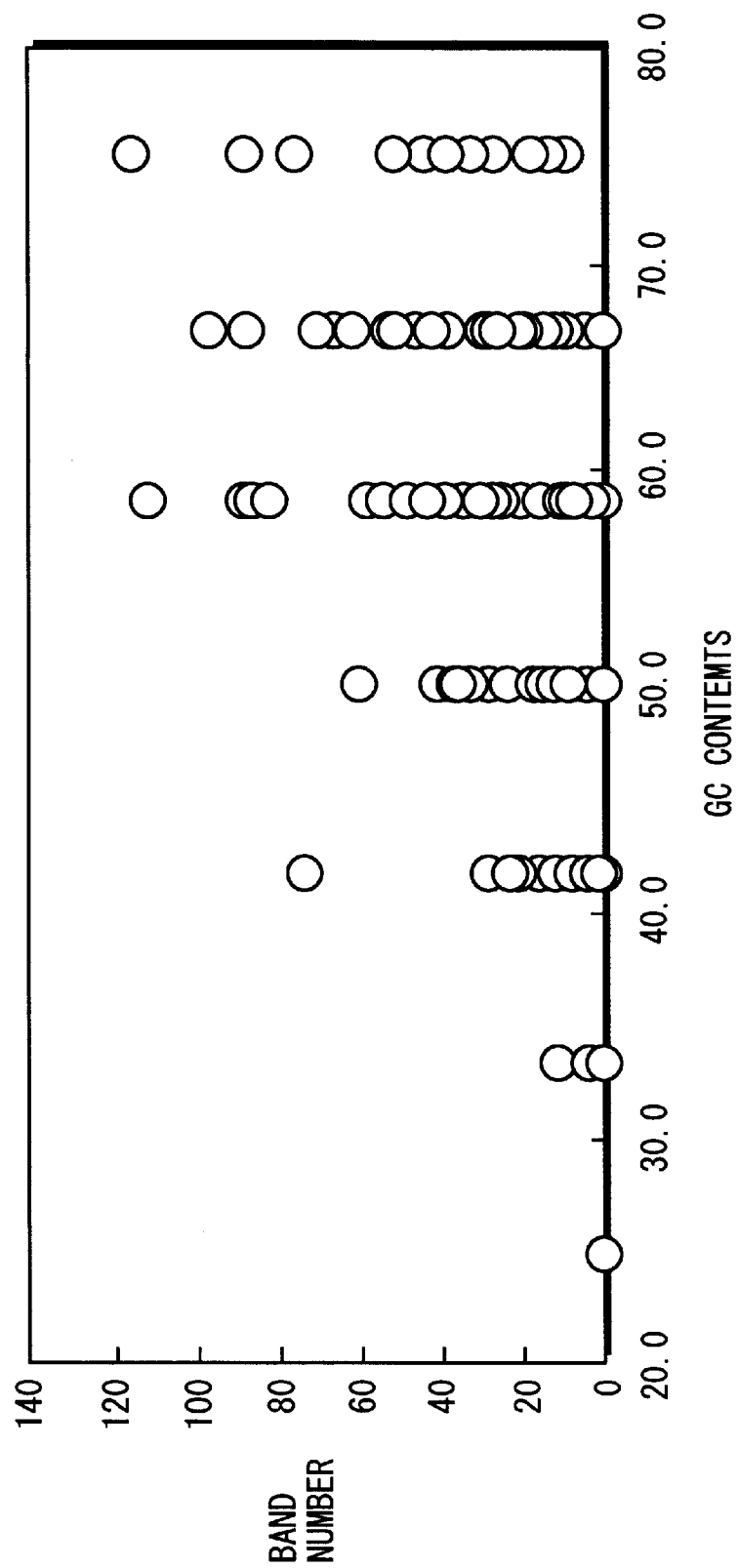
FIG. 11 illustrates band numbers for GC contents of 216 primers.

FIG. 11 illustrates band numbers (total band numbers) for the GC contents of the 216 primers. Tables 8 to 15 also show the GC contents of the primers. As shown in FIG. 11, positive correlation is observed between the GC contents and the band numbers, and such a tendency has been confirmed that the band number increases in proportion to the GC content.

Referring to FIGS. 9 and 10, the band number corresponding to each primer indicates the amplification probability of the primer. The genome size of bacteria is about $5 \times 10^6$ bp, for example, and hence it is estimated that a DNA fragment is amplified for $10^6$ bp if the band number (total band number) confirmed from seven bacteria is 3.5. When arranging the primers in the openings 51 of the apparatus for amplifying DNA fragments shown in FIGS. 4 or 5 on the basis of the band numbers shown in FIGS. 9 and 10, therefore, a plurality of microorganisms contained in a microorganism flora can be effectively discriminated.

In this Example, 94 primers in total were selected from those having band numbers of 1 to 11, those having band numbers of 0 and GC contents in the range of 40 to 60% and those having band numbers of 20, and arranged in the apparatus for amplifying DNA fragments shown in FIGS. 4 or 5 substantially in order of the amplification probabilities. The 94 primers as selected had sequence Nos. 21 to 38, 42 to 115, 117 and 141. Referring to FIG. 5, a combination of chromosome DNA of the bacterium No. 10 in Table 3 and the primer having the sequence No. 69 was employed as the positive control, while the primer of the sequence No. 69 was employed as the negative control.

The selected primers are not restricted to the above but those having large band numbers can be selected from Tables 8 to 15 for assaying a microorganism flora formed by a small number of types of microorganisms while primers having small band numbers can be selected from Tables 8 to 15 when assaying a microorganism flora formed by a large number of types of microorganisms, for example.

Example 2

Then, a group of microorganisms, particularly bacteria contained in the tank of a garbage disposal were analyzed by the inventive method of assaying a group of microorganisms with the 94 types of primers (sequence Nos. 21 to 38, 42 to 115, 117 and 141) selected in Example 1.

① DNA Analysis of Bacterium No.10 Isolated from Garbage Disposal

In this Example, the bacterium No. 10 in Table 3 isolated from the tank of the garbage disposal in Example 1 was employed as a sample and chromosome DNA of this bacterium was prepared. The bacterium No. 10 was isolated and the chromosome DNA was prepared by methods similar to those described with reference to Example 1.

Then, reaction solutions for random PCR were prepared with the chromosome DNA of the bacterium No. 10. The composition of the reaction solutions for random PCR is shown in Table 6 for Example 1. In this case, 94 types of reaction solutions for random PCR containing the 94 primers of the sequence Nos. 21 to 38, 42 to 115, 117 and 141 respectively were simultaneously prepared. Further, a reaction solution containing the primer of the sequence No. 69 and template DNA having a base sequence corresponding thereto was prepared as the positive control while a reaction solution containing the primer of the sequence No. 69 with no DNA was prepared as the negative control simultaneously with the 94 types of reaction solutions for random PCR.

Then, the 94 types of reaction solutions for random PCR were stored in the 94 openings 51 of the apparatus for amplifying DNA fragments shown in FIG. 5, while the negative control and the positive control were stored in the openings 51a and 51b respectively. Random PCR was performed with the apparatus for amplifying DNA fragments, and thereafter the reaction solutions were analyzed by electrophoresis. Electrophoretic patterns thus obtained were stained and photographed. The random PCR, the electrophoresis and the staining of the electrophoretic patterns and photographing after the electrophoresis are identical to those described with reference to Example 1.

In the electrophoretic patterns obtained by the electrophoresis, 14 clear bands (DNA fragments) appeared as to nine types of primers. No band was confirmed in relation to the negative control. Thus, it has been possible to confirm that the appearing bands belonged to the bacterium No. 10. Further, the luminous intensity of a band of the positive control was measured for correcting those of the remaining bands on the basis thereof. If the measured luminous intensity of the band of the positive control is 70%, for example, the luminous intensity of this band is corrected to be 100% while those of the remaining bands are also corrected in similar ratios. Thus, influence exerted on the amplification efficiency for the DNA fragments by errors of reaction conditions etc. in DNA fragment amplification was eliminated.

Figure 12:
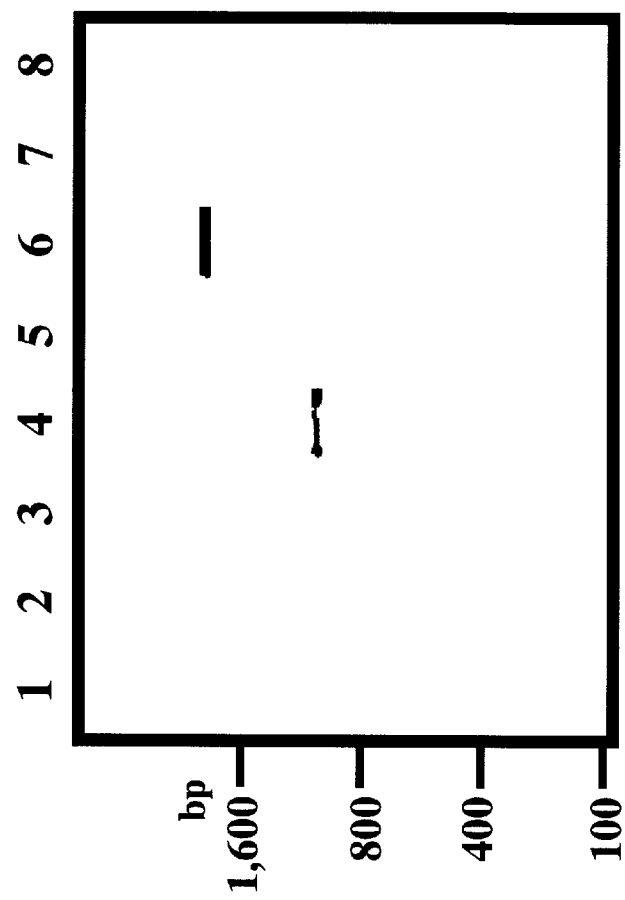
FIG. 12 shows an electrophoretic pattern of a DNA fragment amplified from chromosome DNA of an isolated bacterium with primers of sequence Nos. 64 to 71.

FIG. 12 shows an electrophoretic pattern as to eight types of primers of the sequence Nos. 64 to 71 among the 94 types of primers. Numerals 1 to 8 on the horizontal axis of the electrophoretic pattern in FIG. 12 denote the primers of the sequence Nos. 64 to 71 respectively.

As shown in FIG. 12, a single band appeared in each of the primers of the sequence Nos. 67 and 69. Thus, it was indicated that DNA fragments of the bacterium No. 10 were amplified by the primers of the sequence Nos. 67 and 69. From the positions of the appearing bands, further, it was estimated that the amplified DNA fragments were about 990 bp and about 1800 bp in size.

② DNA Analysis of Five Types of Bacteria Isolated from Garbage Disposal

In this Example, five types of bacteria isolated from the garbage disposal on the 490$^{th}$ day from starting driving were employed as samples, and chromosome DNA was prepared from each bacterium. The five types of bacteria were isolated and the chromosome DNA was prepared by methods similar to those described with reference to Example 1.

Then, a chromosome DNA mixture of the five types of bacteria was prepared by mixing the chromosome DNA of the prepared bacteria. 94 types of reaction solutions for random PCR were prepared with the chromosome DNA mixture and 94 types of primers, while preparing a positive control and a negative control. The composition of the reaction solutions for random PCR is identical to that shown in Table 6 with reference to Example 1, except that each reaction solution contains 10 pg/μL of chromosome DNA of each bacterium in concentration. Further, random PCR was performed with the reaction solutions for random PCR, the positive control and the negative control, and thereafter the reaction solutions were analyzed by electrophoresis. Thereafter obtained electrophoretic patterns were stained and photographed. The random PCR and the electrophoresis are identical to those described with reference to Example 1. Further, bands were corrected on the basis of amplification efficiency with the positive control by a method similar to that described with reference to ① of example 2.

In the electrophoretic patterns of the reaction solutions for random PCR obtained by the electrophoresis, 85 clear bands appeared in 40 types of primers.

Figure 13:
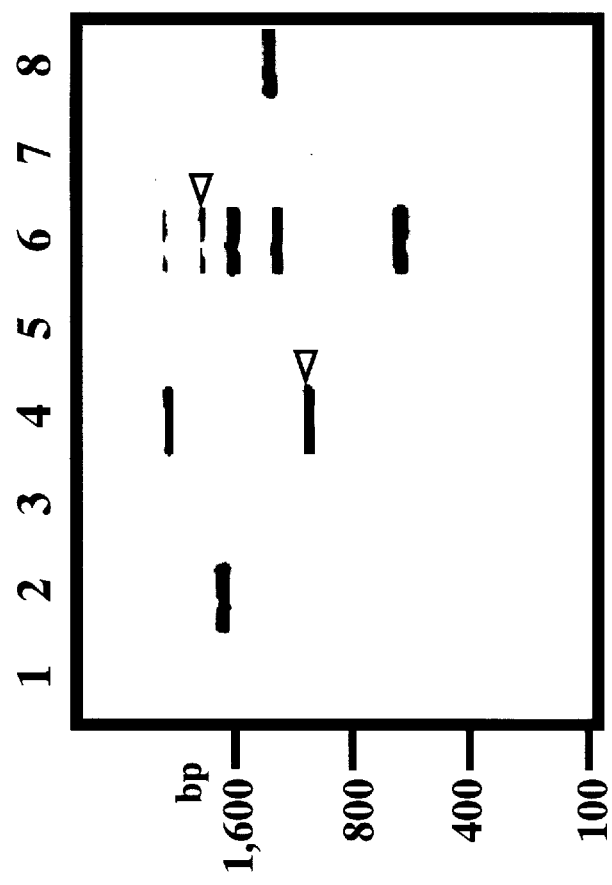
FIG. 13 shows an electrophoretic pattern of DNA fragments amplified from a mixture of chromosome DNA of five types of isolated bacteria with primers of sequence Nos. 64 to 71.

FIG. 13 shows an electrophoretic pattern as to eight types of primers of the sequence Nos. 64 to 71 among the 94 types of primers. Numerals 1 to 8 on the horizontal axis of the electrophoretic pattern shown in FIG. 13 denote the primers of the sequence Nos. 64 to 71 respectively.

As shown in FIG. 13, the number of the bands appearing when employing the chromosome DNA mixture of five types of bacteria was larger than that of the bands appearing when employing the chromosome DNA of the bacterium No. 10 shown in FIG. 12, and nine bands in total appeared in four primers of the sequence Nos. 65, 67, 69 and 71. Thus, the number of the bands appearing when employing five types of bacteria is about five times that of the bands appearing when employing the bacterium No. 10 shown in FIG. 9. The primers of the sequence Nos. 64 to 71 amplify about 0.3 DNA fragments on the average from chromosome DNA of a bacterium. When amplifying chromosome DNA of a bacterium with eight types of primers having such an amplification probability, about two to three (2.4 in calculation) DNA fragments are obtained. Thus, when amplifying chromosome DNA of five types of bacteria with the above eight types of primers, DNA fragments of five times those amplified from a bacterium, i.e., 12 DNA fragments are obtained in calculation.

Thus, when a plurality of types of bacteria are mixed with each other, DNA fragments are amplified in a number responsive to the number of types of the bacteria. Further, the differences between the types of the bacteria can be detected as the combinations of the primer and the sizes of the DNA fragments amplified with that primer. Therefore, the state of each bacterium forming the bacteria can be readily estimated from the obtained electrophoretic pattern.

In the bands appearing in the primers of the sequence Nos. 69 and 71 shown in FIG. 13, those with arrows matched with the bands appearing in the electrophoretic pattern of the bacterium No. 10 shown in FIG. 9. Thus, it is estimable that the five types of bacteria isolated from the garbage disposal include the bacterium No. 10.

The difference between the number of the actually amplified DNA fragments and the value in calculation results from that the lengths of chromosome DNA vary with the types of the bacteria and from the following:

The four bases are not contained in chromosome DNA of bacteria in the same ratio but the numbers of these bases are unbalanced and the order of sequence of each base is different. Such unbalanced states of the bases vary with the types of the bacteria. When chromosome DNA of a bacterium has unbalanced base sequences, the numbers of DNA fragments amplified by a plurality of primers differ from each other even if the primers have the same amplification probability. The number of amplified DNA fragments is large when employing a primer having a base sequence complementary to that contained in the chromosome DNA in a large number, while the number of amplified DNA fragments is small when employing a primer having a base sequence complementary to that contained in a small number. If the number of types of primers employed for the random PCR method is small, therefore, sufficient information cannot be obtained due to unbalanced types of the amplified DNA fragments.

For example, the primer of the sequence No. 67 amplifies a DNA fragment for the single bacterium No. 10, while amplifying two DNA fragments for the five types of bacteria. On the other hand, the primer of the sequence No. 69 amplifies a DNA fragment for the single bacterium No. 10, while amplifying five DNA fragments for the five types of bacteria. Thus, the number of types of bacteria and the number of DNA fragments are correlated in the primer of the sequence No. 69, while no correlation is observed between the number of types of bacteria and the number of DNA fragments in the primer of the sequence No. 67. This is because the five types of bacteria contain the base sequence complementary to the primer of the sequence No. 69 in a large number, while only the bacterium No. 10 contains the base sequence complementary to the primer of sequence No. 67 in a large number and the remaining four types of bacteria contain the base sequence complementary thereto in a small number. When employing a plurality of primers, on the contrary, DNA fragments are obtained from the plurality of primers and hence the total number of obtained bands approaches the value in calculation obtained from the types of the bacteria, the types of the primers and the amplification probabilities of the primers as a whole. Thus, the number of types of bacteria can be estimated from the total number of amplified DNA fragments. Also when employing about eight types of primers, the total number of amplified DNA fragments reflected the number of types of the bacteria, as described above.

③ Analysis of Bacteria in Garbage Disposal

In this Example, 10 g of wood chips were sampled from the tank of a garbage disposal on the 150$^{th}$ day from starting driving. 90 mL of a sterilized 0.85% salt solution was added to the wood chips and thereafter bacteria were isolated from the wood chips by a suspension method. In this case, a masticator by Gunze Sangyo, Ltd. was employed as a suspension apparatus for performing treatment for one minute. Thereafter the treated solution was filtered through a coarse prefilter (stoma filter by Gunze Sangyo, Ltd.). Further, the solution was successively filtered through membrane filters of 25 $\mu$m and 5 $\mu$m.

Figure 14:
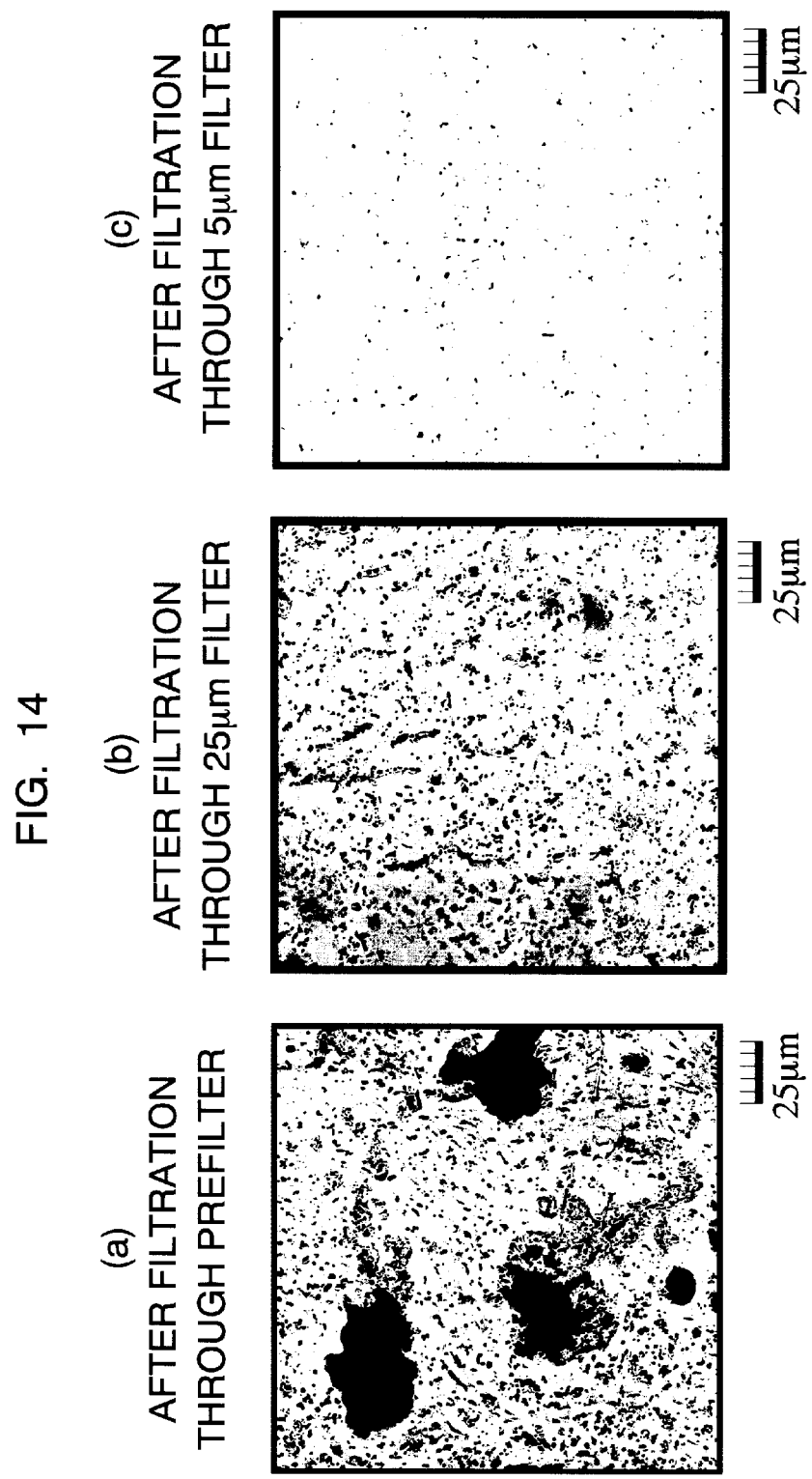
FIG. 14 shows states of a filtrate observed with a microscope in filtration steps.

FIG. 14 shows states of the filtrate observed with a microscope in the above filtration steps. Referring to FIG. 14, (a) shows the state of the filtrate filtered through the prefilter, and (b) shows the state after filtration through the membrane filter of 25 $\mu$m. Further, (c) shows the state after filtration through the membrane filter of 5 $\mu$m.

As shown at (a) in FIG. 14, the filtrate contained foreign matter exceeding 25 $\mu$m such as the kitchen garbage in the process of degradation and bits of wood and microorganisms such as protozoa larger then the bacteria after filtration through the coarse prefilter. When filtering this filtrate through the membrane filter of 25 $\mu$m, the large foreign matter was removed as shown at (b) in FIG. 14. This filtrate still contained large cells, conceivably protozoa, exceeding 10 $\mu$m. When further filtering this filtrate through the membrane filter of 5 $\mu$m, the large cells were removed while small dots remained. These small dots, exhibiting bacterial motion in observation with a microscope, were confirmed to be bacteria.

Thus, it was possible to efficiently gather bacteria by filtration through membrane filters.

Then, the filtrate filtered through the membrane filter of 5 $\mu$m was centrifuged by 1800 g for 15 minutes, to recover a pellet formed by precipitation of the bacteria. Thus, bacteria were extracted from the tank of the garbage disposal.

Then, chromosome DNA of the extracted bacteria was extracted by a method similar to that in Example 1, and dissolved in 50 $\mu$L of a mixed solution (hereinafter referred to as TE solution) of 10 mM of Tris-HCl (pH 8.0) and 1 mM of ethylenediamine-N, N, N', N'-tetraacetic acid (EDTA). Thus prepared was a TE solution of a chromosome DNA mixture containing chromosome DNA of a plurality of different types of bacteria.

Then, reaction solutions for random PCR were prepared with the chromosome DNA mixture while preparing a positive control and a negative control. The compositions of the reaction solutions for random PCR, the positive control and the negative control are identical to those described with reference to ① of Example 2. In this case, 0.02 $\mu$L of the TE solution of the chromosome DNA mixture was added to 20 $\mu$L of each reaction solution for random PCR.

Random PCR was performed with the apparatus for amplifying DNA fragments shown in FIG. 5, and thereafter the reaction solutions were analyzed by electrophoresis. The random PCR and the electrophoresis are identical to those described with reference to Example 1. In this case, a quantitatively analyzable DNA size marker ($\lambda$/Hind III and BioLad Amplisize Standard) having a known concentration was electrophoresed simultaneously with the reaction solutions.

Figure 15:
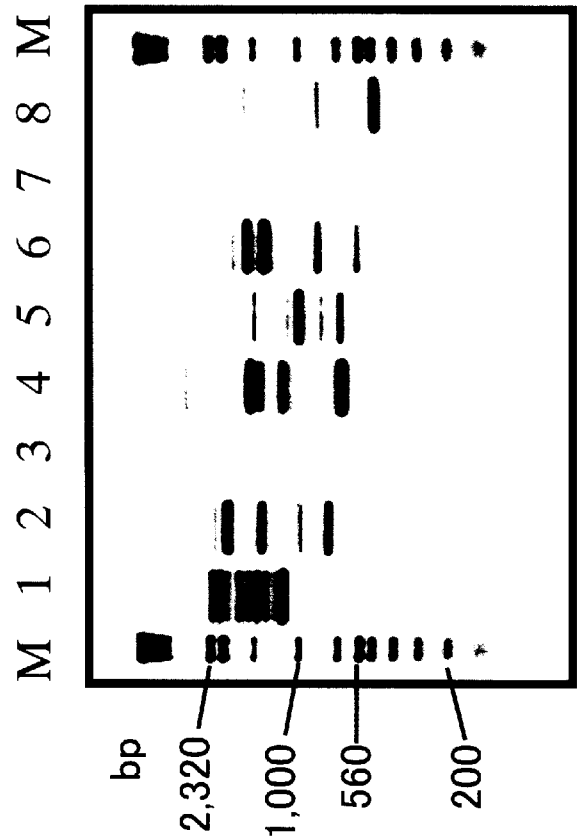
FIG. 15 shows an electrophoretic pattern of DNA fragments amplified from chromosome DNA of microorganisms contained in the tank of a garbage disposal with primers of sequence Nos. 64 to 71.

After the electrophoresis, obtained electrophoretic patterns were stained with ethidium bromide for acquiring ethidium bromide fluorescent images irradiated with ultraviolet light of 254 nm in wavelength with a Polaroid camera or a CCD camera. In this case, the electrophoretic images were acquired as to the first to 12$^{th}$ lanes of the apparatus for amplifying DNA fragments, to obtain 12 electrophoretic photographs Nos. 1 to 12. Each electrophoretic photograph shows electrophoretic images of eight types of different primers and the DNA size marker. FIG. 15 shows the electrophoretic photograph No. 6 among those obtained in the aforementioned manner.

FIG. 15 shows the electrophoretic photograph No. 6 on the sixth lane of the apparatus for amplifying DNA fragments with electrophoretic images of the eight types of primers of the sequence Nos. 64 to 71. Referring to FIG. 15, symbol M denotes the electrophoretic image of the DNA size marker, and numerals 1 to 8 on the horizontal axis denote the primers of the sequence Nos. 64 to 71 respectively.

As shown in FIG. 15, a plurality of bands appeared in each of the primers of the sequence Nos. 64, 65, 67, 68, 69 and 71.

Each of the electrophoretic photographs Nos. 1 to 12 was incorporated in a computer with a scanner, and thereafter the luminous intensities of the bands in the DNA size marker M at 560 bp and each primer were measured with software (Genomic Solutions Advance Quantifier I-D Match). Further, amplification efficiency for the DNA fragments was obtained from the positive control by a method similar to that described with reference to ① of Example 2, for correcting the bands of the reaction solutions for random PCR on the basis thereof.

In each electrophoretic photograph, the bands of the DNA size marker M were so corrected that the luminous intensities obtained by measurement were 100%, while the luminous intensities of the remaining bands were also corrected in a similar ratio. Errors in gradient can be eliminated in each electrophoretic photograph by thus correcting the gradient of the electrophoretic photograph.

A luminous intensity half that of the band of the DNA size marker M at 560 bp obtained by measurement was set as the threshold, for removing bands having luminous intensities less than the threshold in each primer. When thus removing bands having small luminous intensities, bands having low reproducibility in random PCR are removed for improving the reproducibility in random PCR. Thus, the reliability of the obtained data is improved.

Table 16 shows the numbers of bands having luminous intensities exceeding the threshold in the respective electrophoretic photographs.

TABLE 16

| Photo No. | Corresponding Lane of DNA Amplifier | Band Intensity of DNA Size Marker of 560 bp | Total Number of Bands having intensity exceeding Threshold |
|---|---|---|---|
| 1 | 1$^{st}$ lane | 0.155 | 3 |
| 2 | 2$^{nd}$ lane | 0.265 | 7 |
| 3 | 3$^{rd}$ lane | 0.305 | 22 |
| 4 | 4$^{th}$ lane | 0.260 | 9 |
| 5 | 5$^{th}$ lane | 0.335 | 18 |
| 6 | 6$^{th}$ lane | 0.315 | 20 |
| 7 | 7$^{th}$ lane | 0.320 | 26 |
| 8 | 8$^{th}$ lane | 0.325 | 37 |
| 9 | 9$^{th}$ lane | 0.345 | 38 |
| 10 | 10$^{th}$ lane | 0.240 | 52 |
| 11 | 11$^{th}$ lane | 0.335 | 35 |
| 12 | 12$^{th}$ lane | 0.255 | 42 |

As shown in Table 16, such a tendency was recognized that the number of amplified DNA fragments increases in proportion to the number allotted to the photograph. Thus, it has been suggested that employment of a plurality of primers having a low amplification probability arranged on upper lanes of the apparatus for amplifying DNA fragments is effective when a large number of types of bacteria form the bacteria flora or when analyzing bacteria having large-sized chromosome DNA while employment of a plurality of primers having a high amplification probability arranged on lower lanes of the apparatus for amplifying DNA fragments is effective when a small number of types of bacteria form the bacteria flora or when analyzing bacteria having small-sized chromosome DNA.

As described in the above Examples, it is possible to simultaneously amplify DNA fragments from a plurality of microorganisms forming a microorganism flora with each of a plurality of primers having different amplification probabilities or different orders of amplification probabilities. Thus, an electrophoretic image amplified at the optimum amplification probability can be obtained for every microorganism with no information as to the number of the microorganisms forming the microorganism flora or the size of the chromosomes thereof. Further, the plurality of microorganisms contained in the microorganism flora can be discriminated by analyzing the electrophoretic images.

Consequently, various microorganic ecosystems can be correctly assayed in a short time.

Further, time change of the number of types of the microorganisms forming the microorganism flora can be assayed by assaying the microorganisms in time.

When discriminating the type of the microorganism and analyzing the band pattern of its chromosome DNA as to each of a plurality of microorganisms and establishing a database with the obtained data of the band pattern of the chromosome DNA of each microorganism, the types of the microorganisms forming the microorganism flora can be retrieved from the database by searching the database on the basis of the DNA band patterns of the microorganisms analyzed in the aforementioned manner.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A method of amplifying DNA fragments in a population of DNA molecules obtained from a source, the method comprising:

preparing a plurality of primers selected to have proper amplification probabilities, as assessed using an electrophoretic pattern produced by amplification of DNA obtained from a similar source; and simultaneously applying a polymerase chain reaction (PCR) method to a plurality of different DNAs with each of said plurality of primers, thereby amplifying fragments of said plurality of different DNAs.

2. The method of claim 1, further comprising employing a reference primer having a known sequence and applying said PCR method to a reference DNA having a sequence complementary to the sequence of said reference primer, thereby amplifying a fragment of said reference DNA simultaneously with amplifying said fragments of said plurality of different DNAs.

3. The method of claim 1, further comprising classifying said fragments amplified from said plurality of different DNAs by a discrimination method.

4. The method of claim 3, wherein said discrimination method is electrophoresis.

5. An apparatus for amplifying DNA fragments, comprising:

a body having a plurality of wells; and a plurality of primers having proper amplification probabilities individually arranged in said plurality of wells.

6. A method of assaying a group of microorganisms obtained from a source, the method comprising:

preparing a plurality of primers selected to have proper amplification probabilities, as assessed using an electrophoretic pattern produced by amplification of DNA obtained from a similar source;

simultaneously applying a PCR method to DNA of a plurality of different microorganisms with each of said plurality of primers, thereby amplifying fragments of said DNA of said microorganisms; and classifying said amplified fragments by a discrimination method for discriminating a plurality of different microorganisms included in said group of microorganisms.

7. The method of claim 6, further comprising:

employing a reference primer having a known sequence and applying said PCR method to reference DNA having a sequence complementary to the sequence of said reference primer, thereby amplifying a reference fragment of said reference DNA simultanously with amplifying said fragments of said DNA of said plurality of different microorganisms;

classifying said reference fragment along with said fragments amplified from said DNA of said plurality of different microorganisms by said discrimination method;

obtaining amplification efficiency for said reference DNA on the basis of the result of classification of said reference fragment; and correcting the results of classification of said fragments amplified from said DNA of said plurality of different microorganisms on the basis of said amplification efficiency.

8. The method of claim 7, wherein said discrimination method is electrophoresis.

9. The method of claim 8, further comprising:

employing a DNA size marker with said fragments amplified from said DNA of said plurality of different microorganisms for said electrophoresis;

staining an electrophoretic pattern obtained by said electrophoresis; and correcting the gradient of said electrophoretic pattern based on the luminous intensity of said DNA size marker in said stained electrophoretic pattern.

10. The method of claim 9, further comprising:

setting a threshold based on the luminous intensity of said DNA size marker in said electrophoretic pattern; and analyzing said group of microorganisms on the basis of a band having a luminous intensity exceeding said threshold in said electrophoretic pattern.

11. The method of claim 6, further comprising:

isolating a bacterium;

applying said PCR method to said isolated bacterium with each of said plurality of primers, thereby amplifying a bacterial fragment of DNA from said bacterium;

classifying said bacterial fragment by said discrimination method; and analyzing the results of discrimination of said amplified fragments from said DNA of said plurality of different microorganisms based on the classification of said bacterial fragment.

12. A method of analyzing groups of microorganisms obtained from a source, the method comprising:

preparing a plurality of primers selected to have proper amplification probabilities as assessed by an electrophoretic pattern produced by amplification of DNA obtained from a similar source;

simultaneously applying a PCR method to DNA of a plurality of different microorganisms included in a first group of microorganisms with each of said plurality of primers, thereby amplifying fragments of said first group;

classifying said amplified DNA fragments of said first group by a discrimination method;

simultaneously applying said PCR method to DNA of a plurality of different microorganisms included in a second group of microorganisms with each of said plurality of primers, thereby amplifying fragments of said DNA of said second group;

classifying said amplified DNA fragments of said second group by said discrimination method; and comparing the results of classification of said first group of microorganisms with those of said second group of microorganisms.

13. The method of claim 12, wherein said discrimination method is electrophoresis.

14. A method of analyzing groups of microorganisms obtained from a source, the method comprising:

sampling a group of microorganisms at a plurality of points of time;

simultaneously applying a PCR method to DNA of a plurality of different microorganisms included in said group with each of a plurality of primers, wherein the primers are selected to have proper amplification probabilities, as assessed using an electrophoretic pattern produced by amplification of DNA obtained from a similar source, thereby amplifying fragments of said DNA of said group;

classifying said amplified DNA fragments by a discrimination method; and analyzing time change of the state of said group of microorganisms on the basis of the results of classification at said plurality of points of time.

15. The method of claim 14, wherein said discrimination method is electrophoresis.

16. A method of assaying a contaminant material obtained from a first source, the method comprising:

applying a PCR method to DNA of a microorganism related to said contaminant material with each of a plurality of primers, wherein the primers are selected to have proper amplification probabilities, as assessed using an electrophoretic pattern produced by amplification of DNA obtained from a similar source, thereby amplifying a DNA fragment of said contaminant material;

classifying said DNA fragment by a discrimination method;

preserving the relation between the type of said microorganism and the result of classification in a database;

simultaneously applying said PCR method to DNA of a plurality of different microorganisms obtained from the first source with each of said plurality of primers thereby amplifying first fragments of said DNA of said plurality of different microorganisms;

classifying said first fragments amplified by said discrimination method; and retrieving the types of said plurality of different microorganisms from said database on the basis of the results of classification of said first fragments.

17. The method of claim 16, further comprising determining presence/absence of said contaminant material obtained from said similar source on the basis of the results of retrieval of said database.

18. The method of claim 16, further comprising determining the quantity of said contaminant material present in said similar source on the basis of the results of retrieval of said database.

19. The method of claim 16, wherein said database preserves a plurality of types of microorganisms and results of classification corresponding thereto.

20. The method of claim 16, wherein said discrimination method is electrophoresis, said results of classification are band patterns produced from an electrophoretic pattern, and said database preserves the relation between the type of microorganism and band patterns produced from said electrophoretic pattern.

21. The method of claim 6, wherein said discrimination method is electrophoresis, the method further comprising:

staining an electrophoretic pattern obtained by said electrophoresis; and correcting the gradient of said electrophoretic pattern based on the luminous intensity of said reference fragment in said stained electrophoretic pattern.

22. The method of claim 21, further comprising:

setting a threshold based on the luminous intensity of said reference fragment in said electrophoretic pattern; and analyzing said group of microorganisms on the basis of a band having a luminous intensity exceeding said threshold in said electrophoretic pattern.

* * * * *

SEQUENCE LISTING

```
<160> NUMBER OF SEQ ID NOS: 216

<210> SEQ ID NO 1
<211> LENGTH: 12
<212> TYPE: DNA
<213> ORGANISM: Artificial Sequence
<220> FEATURE:
<223> OTHER INFORMATION: Primer

<400> SEQUENCE: 1
actgagaaaa ta                                                          12

<210> SEQ ID NO 2
<211> LENGTH: 12
<212> TYPE: DNA
<213> ORGANISM: Artificial Sequence
<220> FEATURE:
<223> OTHER INFORMATION: Primer

<400> SEQUENCE: 2
atcttcaaag at                                                          12

<210> SEQ ID NO 3
<211> LENGTH: 12
<212> TYPE: DNA
<213> ORGANISM: Artificial Sequence
<220> FEATURE:
<223> OTHER INFORMATION: Primer

<400> SEQUENCE: 3
acaaagagat at                                                          12

<210> SEQ ID NO 4
<211> LENGTH: 12
<212> TYPE: DNA
<213> ORGANISM: Artificial Sequence
<220> FEATURE:
<223> OTHER INFORMATION: Primer

<400> SEQUENCE: 4
gaggtgatat ta                                                          12
```

```
<210> SEQ ID NO 5
<211> LENGTH: 12
<212> TYPE: DNA
<213> ORGANISM: Artificial Sequence
<220> FEATURE:
<223> OTHER INFORMATION: Primer

<400> SEQUENCE: 5
atcttctcat ct                                                    12

<210> SEQ ID NO 6
<211> LENGTH: 12
<212> TYPE: DNA
<213> ORGANISM: Artificial Sequence
<220> FEATURE:
<223> OTHER INFORMATION: Primer

<400> SEQUENCE: 6
actcttctac aa                                                    12

<210> SEQ ID NO 7
<211> LENGTH: 12
<212> TYPE: DNA
<213> ORGANISM: Artificial Sequence
<220> FEATURE:
<223> OTHER INFORMATION: Primer

<400> SEQUENCE: 7
agagacatag tt                                                    12

<210> SEQ ID NO 8
<211> LENGTH: 12
<212> TYPE: DNA
<213> ORGANISM: Artificial Sequence
<220> FEATURE:
<223> OTHER INFORMATION: Primer

<400> SEQUENCE: 8
gccagatata ta                                                    12

<210> SEQ ID NO 9
<211> LENGTH: 12
<212> TYPE: DNA
<213> ORGANISM: Artificial Sequence
<220> FEATURE:
<223> OTHER INFORMATION: Primer

<400> SEQUENCE: 9
cacactactt at                                                    12

<210> SEQ ID NO 10
<211> LENGTH: 12
<212> TYPE: DNA
<213> ORGANISM: Artificial Sequence
<220> FEATURE:
<223> OTHER INFORMATION: Primer

<400> SEQUENCE: 10
atgagaaagg aa                                                    12

<210> SEQ ID NO 11
<211> LENGTH: 12
<212> TYPE: DNA
<213> ORGANISM: Artificial Sequence
<220> FEATURE:
```

```
<223> OTHER INFORMATION: Primer

<400> SEQUENCE: 11
atcaacactt tc                                                          12

<210> SEQ ID NO 12
<211> LENGTH: 12
<212> TYPE: DNA
<213> ORGANISM: Artificial Sequence
<220> FEATURE:
<223> OTHER INFORMATION: Primer

<400> SEQUENCE: 12
gagactacaa ta                                                          12

<210> SEQ ID NO 13
<211> LENGTH: 12
<212> TYPE: DNA
<213> ORGANISM: Artificial Sequence
<220> FEATURE:
<223> OTHER INFORMATION: Primer

<400> SEQUENCE: 13
ccatacatat tg                                                          12

<210> SEQ ID NO 14
<211> LENGTH: 12
<212> TYPE: DNA
<213> ORGANISM: Artificial Sequence
<220> FEATURE:
<223> OTHER INFORMATION: Primer

<400> SEQUENCE: 14
gatactgatg at                                                          12

<210> SEQ ID NO 15
<211> LENGTH: 12
<212> TYPE: DNA
<213> ORGANISM: Artificial Sequence
<220> FEATURE:
<223> OTHER INFORMATION: Primer

<400> SEQUENCE: 15
agattcttac tg                                                          12

<210> SEQ ID NO 16
<211> LENGTH: 12
<212> TYPE: DNA
<213> ORGANISM: Artificial Sequence
<220> FEATURE:
<223> OTHER INFORMATION: Primer

<400> SEQUENCE: 16
agcccttatt ta                                                          12

<210> SEQ ID NO 17
<211> LENGTH: 12
<212> TYPE: DNA
<213> ORGANISM: Artificial Sequence
<220> FEATURE:
<223> OTHER INFORMATION: Primer

<400> SEQUENCE: 17
gagactatga aa                                                          12
```

```
<210> SEQ ID NO 18
<211> LENGTH: 12
<212> TYPE: DNA
<213> ORGANISM: Artificial Sequence
<220> FEATURE:
<223> OTHER INFORMATION: Primer

<400> SEQUENCE: 18
atcaagtatc ca                                                            12

<210> SEQ ID NO 19
<211> LENGTH: 12
<212> TYPE: DNA
<213> ORGANISM: Artificial Sequence
<220> FEATURE:
<223> OTHER INFORMATION: Primer

<400> SEQUENCE: 19
actgacctag tt                                                            12

<210> SEQ ID NO 20
<211> LENGTH: 12
<212> TYPE: DNA
<213> ORGANISM: Artificial Sequence
<220> FEATURE:
<223> OTHER INFORMATION: Primer

<400> SEQUENCE: 20
atttggatag gg                                                            12

<210> SEQ ID NO 21
<211> LENGTH: 12
<212> TYPE: DNA
<213> ORGANISM: Artificial Sequence
<220> FEATURE:
<223> OTHER INFORMATION: Primer

<400> SEQUENCE: 21
gactgctata ca                                                            12

<210> SEQ ID NO 22
<211> LENGTH: 12
<212> TYPE: DNA
<213> ORGANISM: Artificial Sequence
<220> FEATURE:
<223> OTHER INFORMATION: Primer

<400> SEQUENCE: 22
tggtacggta ta                                                            12

<210> SEQ ID NO 23
<211> LENGTH: 12
<212> TYPE: DNA
<213> ORGANISM: Artificial Sequence
<220> FEATURE:
<223> OTHER INFORMATION: Primer

<400> SEQUENCE: 23
tactactgtg ga                                                            12

<210> SEQ ID NO 24
<211> LENGTH: 12
<212> TYPE: DNA
<213> ORGANISM: Artificial Sequence
<220> FEATURE:
<223> OTHER INFORMATION: Primer
```

-continued

```
<400> SEQUENCE: 24
tggctgtaga aa                                                             12

<210> SEQ ID NO 25
<211> LENGTH: 12
<212> TYPE: DNA
<213> ORGANISM: Artificial Sequence
<220> FEATURE:
<223> OTHER INFORMATION: Primer

<400> SEQUENCE: 25
tctacacgaa gt                                                             12

<210> SEQ ID NO 26
<211> LENGTH: 12
<212> TYPE: DNA
<213> ORGANISM: Artificial Sequence
<220> FEATURE:
<223> OTHER INFORMATION: Primer

<400> SEQUENCE: 26
ccagattttc tg                                                             12

<210> SEQ ID NO 27
<211> LENGTH: 12
<212> TYPE: DNA
<213> ORGANISM: Artificial Sequence
<220> FEATURE:
<223> OTHER INFORMATION: Primer

<400> SEQUENCE: 27
atcaacgtac gt                                                             12

<210> SEQ ID NO 28
<211> LENGTH: 12
<212> TYPE: DNA
<213> ORGANISM: Artificial Sequence
<220> FEATURE:
<223> OTHER INFORMATION: Primer

<400> SEQUENCE: 28
ttccgtaatc ac                                                             12

<210> SEQ ID NO 29
<211> LENGTH: 12
<212> TYPE: DNA
<213> ORGANISM: Artificial Sequence
<220> FEATURE:
<223> OTHER INFORMATION: Primer

<400> SEQUENCE: 29
gcttacatag ac                                                             12

<210> SEQ ID NO 30
<211> LENGTH: 12
<212> TYPE: DNA
<213> ORGANISM: Artificial Sequence
<220> FEATURE:
<223> OTHER INFORMATION: Primer

<400> SEQUENCE: 30
actccaaatg tg                                                             12

<210> SEQ ID NO 31
<211> LENGTH: 12
```

```
<212> TYPE: DNA
<213> ORGANISM: Artificial Sequence
<220> FEATURE:
<223> OTHER INFORMATION: Primer

<400> SEQUENCE: 31
aagtcgtttg gg                                                            12

<210> SEQ ID NO 32
<211> LENGTH: 12
<212> TYPE: DNA
<213> ORGANISM: Artificial Sequence
<220> FEATURE:
<223> OTHER INFORMATION: Primer

<400> SEQUENCE: 32
ctagtatggg ac                                                            12

<210> SEQ ID NO 33
<211> LENGTH: 12
<212> TYPE: DNA
<213> ORGANISM: Artificial Sequence
<220> FEATURE:
<223> OTHER INFORMATION: Primer

<400> SEQUENCE: 33
gagttcgaac ga                                                            12

<210> SEQ ID NO 34
<211> LENGTH: 12
<212> TYPE: DNA
<213> ORGANISM: Artificial Sequence
<220> FEATURE:
<223> OTHER INFORMATION: Primer

<400> SEQUENCE: 34
actttcctac gg                                                            12

<210> SEQ ID NO 35
<211> LENGTH: 12
<212> TYPE: DNA
<213> ORGANISM: Artificial Sequence
<220> FEATURE:
<223> OTHER INFORMATION: Primer

<400> SEQUENCE: 35
ttcccgtcta tc                                                            12

<210> SEQ ID NO 36
<211> LENGTH: 12
<212> TYPE: DNA
<213> ORGANISM: Artificial Sequence
<220> FEATURE:
<223> OTHER INFORMATION: Primer

<400> SEQUENCE: 36
agccttacgg ca                                                            12

<210> SEQ ID NO 37
<211> LENGTH: 12
<212> TYPE: DNA
<213> ORGANISM: Artificial Sequence
<220> FEATURE:
<223> OTHER INFORMATION: Primer

<400> SEQUENCE: 37
```
gctatggcaa cg                                                              12

<210> SEQ ID NO 38
<211> LENGTH: 12
<212> TYPE: DNA
<213> ORGANISM: Artificial Sequence
<220> FEATURE:
<223> OTHER INFORMATION: Primer

<400> SEQUENCE: 38
ccttggaact cg                                                              12

<210> SEQ ID NO 39
<211> LENGTH: 12
<212> TYPE: DNA
<213> ORGANISM: Artificial Sequence
<220> FEATURE:
<223> OTHER INFORMATION: Primer

<400> SEQUENCE: 39
tctgctgacc gg                                                              12

<210> SEQ ID NO 40
<211> LENGTH: 12
<212> TYPE: DNA
<213> ORGANISM: Artificial Sequence
<220> FEATURE:
<223> OTHER INFORMATION: Primer

<400> SEQUENCE: 40
ggcaactggc ca                                                              12

<210> SEQ ID NO 41
<211> LENGTH: 12
<212> TYPE: DNA
<213> ORGANISM: Artificial Sequence
<220> FEATURE:
<223> OTHER INFORMATION: Primer

<400> SEQUENCE: 41
gtcattaaag ct                                                              12

<210> SEQ ID NO 42
<211> LENGTH: 12
<212> TYPE: DNA
<213> ORGANISM: Artificial Sequence
<220> FEATURE:
<223> OTHER INFORMATION: Primer

<400> SEQUENCE: 42 tacactttg ac                                                               12

<210> SEQ ID NO 43
<211> LENGTH: 12
<212> TYPE: DNA
<213> ORGANISM: Artificial Sequence
<220> FEATURE:
<223> OTHER INFORMATION: Primer

<400> SEQUENCE: 43
tggatctttg ac                                                              12

<210> SEQ ID NO 44
<211> LENGTH: 12
<212> TYPE: DNA
<213> ORGANISM: Artificial Sequence -continued

```
<220> FEATURE:
<223> OTHER INFORMATION: Primer

<400> SEQUENCE: 44 gctctttttgg aa                                                        12

<210> SEQ ID NO 45
<211> LENGTH: 12
<212> TYPE: DNA
<213> ORGANISM: Artificial Sequence
<220> FEATURE:
<223> OTHER INFORMATION: Primer

<400> SEQUENCE: 45
atcatcgtac gt                                                         12

<210> SEQ ID NO 46
<211> LENGTH: 12
<212> TYPE: DNA
<213> ORGANISM: Artificial Sequence
<220> FEATURE:
<223> OTHER INFORMATION: Primer

<400> SEQUENCE: 46
tacgatatgg ct                                                         12

<210> SEQ ID NO 47
<211> LENGTH: 12
<212> TYPE: DNA
<213> ORGANISM: Artificial Sequence
<220> FEATURE:
<223> OTHER INFORMATION: Primer

<400> SEQUENCE: 47
gatccagtct tt                                                         12

<210> SEQ ID NO 48
<211> LENGTH: 12
<212> TYPE: DNA
<213> ORGANISM: Artificial Sequence
<220> FEATURE:
<223> OTHER INFORMATION: Primer

<400> SEQUENCE: 48
agaatgtccg ta                                                         12

<210> SEQ ID NO 49
<211> LENGTH: 12
<212> TYPE: DNA
<213> ORGANISM: Artificial Sequence
<220> FEATURE:
<223> OTHER INFORMATION: Primer

<400> SEQUENCE: 49
ccgcagttag at                                                         12

<210> SEQ ID NO 50
<211> LENGTH: 12
<212> TYPE: DNA
<213> ORGANISM: Artificial Sequence
<220> FEATURE:
<223> OTHER INFORMATION: Primer

<400> SEQUENCE: 50
cagtgggagt tt                                                         12
```

```
<210> SEQ ID NO 51
<211> LENGTH: 12
<212> TYPE: DNA
<213> ORGANISM: Artificial Sequence
<220> FEATURE:
<223> OTHER INFORMATION: Primer

<400> SEQUENCE: 51
tctatggacc ct                                                            12

<210> SEQ ID NO 52
<211> LENGTH: 12
<212> TYPE: DNA
<213> ORGANISM: Artificial Sequence
<220> FEATURE:
<223> OTHER INFORMATION: Primer

<400> SEQUENCE: 52
ttcattctgg gg                                                            12

<210> SEQ ID NO 53
<211> LENGTH: 12
<212> TYPE: DNA
<213> ORGANISM: Artificial Sequence
<220> FEATURE:
<223> OTHER INFORMATION: Primer

<400> SEQUENCE: 53
ccgtcttttc tg                                                            12

<210> SEQ ID NO 54
<211> LENGTH: 12
<212> TYPE: DNA
<213> ORGANISM: Artificial Sequence
<220> FEATURE:
<223> OTHER INFORMATION: Primer

<400> SEQUENCE: 54
tggcctattg gc                                                            12

<210> SEQ ID NO 55
<211> LENGTH: 12
<212> TYPE: DNA
<213> ORGANISM: Artificial Sequence
<220> FEATURE:
<223> OTHER INFORMATION: Primer

<400> SEQUENCE: 55
gtcatgcctg ga                                                            12

<210> SEQ ID NO 56
<211> LENGTH: 12
<212> TYPE: DNA
<213> ORGANISM: Artificial Sequence
<220> FEATURE:
<223> OTHER INFORMATION: Primer

<400> SEQUENCE: 56
ccttggcgaa gc                                                            12

<210> SEQ ID NO 57
<211> LENGTH: 12
<212> TYPE: DNA
<213> ORGANISM: Artificial Sequence
<220> FEATURE:
<223> OTHER INFORMATION: Primer
```

<400> SEQUENCE: 57
agcctgtggg ct                                                           12

<210> SEQ ID NO 58
<211> LENGTH: 12
<212> TYPE: DNA
<213> ORGANISM: Artificial Sequence
<220> FEATURE:
<223> OTHER INFORMATION: Primer

<400> SEQUENCE: 58
agaattggac ga                                                           12

<210> SEQ ID NO 59
<211> LENGTH: 12
<212> TYPE: DNA
<213> ORGANISM: Artificial Sequence
<220> FEATURE:
<223> OTHER INFORMATION: Primer

<400> SEQUENCE: 59
cttgtcatgt gt                                                           12

<210> SEQ ID NO 60
<211> LENGTH: 12
<212> TYPE: DNA
<213> ORGANISM: Artificial Sequence
<220> FEATURE:
<223> OTHER INFORMATION: Primer

<400> SEQUENCE: 60
tacgtggtaa ca                                                           12

<210> SEQ ID NO 61
<211> LENGTH: 12
<212> TYPE: DNA
<213> ORGANISM: Artificial Sequence
<220> FEATURE:
<223> OTHER INFORMATION: Primer

<400> SEQUENCE: 61
ggacaagtaa tg                                                           12

<210> SEQ ID NO 62
<211> LENGTH: 12
<212> TYPE: DNA
<213> ORGANISM: Artificial Sequence
<220> FEATURE:
<223> OTHER INFORMATION: Primer

<400> SEQUENCE: 62
taccctcaag ct                                                           12

<210> SEQ ID NO 63
<211> LENGTH: 12
<212> TYPE: DNA
<213> ORGANISM: Artificial Sequence
<220> FEATURE:
<223> OTHER INFORMATION: Primer

<400> SEQUENCE: 63
ttcgaggatc ga                                                           12

<210> SEQ ID NO 64

```
<211> LENGTH: 12
<212> TYPE: DNA
<213> ORGANISM: Artificial Sequence
<220> FEATURE:
<223> OTHER INFORMATION: Primer

<400> SEQUENCE: 64
gacctgcgat ct                                                          12

<210> SEQ ID NO 65
<211> LENGTH: 12
<212> TYPE: DNA
<213> ORGANISM: Artificial Sequence
<220> FEATURE:
<223> OTHER INFORMATION: Primer

<400> SEQUENCE: 65
tggcctcttg ga                                                          12

<210> SEQ ID NO 66
<211> LENGTH: 12
<212> TYPE: DNA
<213> ORGANISM: Artificial Sequence
<220> FEATURE:
<223> OTHER INFORMATION: Primer

<400> SEQUENCE: 66
ggtttcccag ga                                                          12

<210> SEQ ID NO 67
<211> LENGTH: 12
<212> TYPE: DNA
<213> ORGANISM: Artificial Sequence
<220> FEATURE:
<223> OTHER INFORMATION: Primer

<400> SEQUENCE: 67
tcgtccggag at                                                          12

<210> SEQ ID NO 68
<211> LENGTH: 12
<212> TYPE: DNA
<213> ORGANISM: Artificial Sequence
<220> FEATURE:
<223> OTHER INFORMATION: Primer

<400> SEQUENCE: 68
cgcttcgtag ca                                                          12

<210> SEQ ID NO 69
<211> LENGTH: 12
<212> TYPE: DNA
<213> ORGANISM: Artificial Sequence
<220> FEATURE:
<223> OTHER INFORMATION: Primer

<400> SEQUENCE: 69
ggcttcgaat cg                                                          12

<210> SEQ ID NO 70
<211> LENGTH: 12
<212> TYPE: DNA
<213> ORGANISM: Artificial Sequence
<220> FEATURE:
<223> OTHER INFORMATION: Primer

<400> SEQUENCE: 70
```

```
gatgagctaa aa                                                               12

<210> SEQ ID NO 71
<211> LENGTH: 12
<212> TYPE: DNA
<213> ORGANISM: Artificial Sequence
<220> FEATURE:
<223> OTHER INFORMATION: Primer

<400> SEQUENCE: 71
gagcaggaat at                                                               12

<210> SEQ ID NO 72
<211> LENGTH: 12
<212> TYPE: DNA
<213> ORGANISM: Artificial Sequence
<220> FEATURE:
<223> OTHER INFORMATION: Primer

<400> SEQUENCE: 72
cttaggttac gt                                                               12

<210> SEQ ID NO 73
<211> LENGTH: 12
<212> TYPE: DNA
<213> ORGANISM: Artificial Sequence
<220> FEATURE:
<223> OTHER INFORMATION: Primer

<400> SEQUENCE: 73
gtggatctga at                                                               12

<210> SEQ ID NO 74
<211> LENGTH: 12
<212> TYPE: DNA
<213> ORGANISM: Artificial Sequence
<220> FEATURE:
<223> OTHER INFORMATION: Primer

<400> SEQUENCE: 74
cctatcccaa ca                                                               12

<210> SEQ ID NO 75
<211> LENGTH: 12
<212> TYPE: DNA
<213> ORGANISM: Artificial Sequence
<220> FEATURE:
<223> OTHER INFORMATION: Primer

<400> SEQUENCE: 75
gagactaccg aa                                                               12

<210> SEQ ID NO 76
<211> LENGTH: 12
<212> TYPE: DNA
<213> ORGANISM: Artificial Sequence
<220> FEATURE:
<223> OTHER INFORMATION: Primer

<400> SEQUENCE: 76
gacagcgtcc ta                                                               12

<210> SEQ ID NO 77
<211> LENGTH: 12
<212> TYPE: DNA
```

```
<213> ORGANISM: Artificial Sequence
<220> FEATURE:
<223> OTHER INFORMATION: Primer

<400> SEQUENCE: 77
cttgagcgta tt                                                        12

<210> SEQ ID NO 78
<211> LENGTH: 12
<212> TYPE: DNA
<213> ORGANISM: Artificial Sequence
<220> FEATURE:
<223> OTHER INFORMATION: Primer

<400> SEQUENCE: 78
actgagatag ca                                                        12

<210> SEQ ID NO 79
<211> LENGTH: 12
<212> TYPE: DNA
<213> ORGANISM: Artificial Sequence
<220> FEATURE:
<223> OTHER INFORMATION: Primer

<400> SEQUENCE: 79
gagagacgat ta                                                        12

<210> SEQ ID NO 80
<211> LENGTH: 12
<212> TYPE: DNA
<213> ORGANISM: Artificial Sequence
<220> FEATURE:
<223> OTHER INFORMATION: Primer

<400> SEQUENCE: 80
gacgcccatt at                                                        12

<210> SEQ ID NO 81
<211> LENGTH: 12
<212> TYPE: DNA
<213> ORGANISM: Artificial Sequence
<220> FEATURE:
<223> OTHER INFORMATION: Primer

<400> SEQUENCE: 81
gacggttcta ca                                                        12

<210> SEQ ID NO 82
<211> LENGTH: 12
<212> TYPE: DNA
<213> ORGANISM: Artificial Sequence
<220> FEATURE:
<223> OTHER INFORMATION: Primer

<400> SEQUENCE: 82
gatggtccgt tt                                                        12

<210> SEQ ID NO 83
<211> LENGTH: 12
<212> TYPE: DNA
<213> ORGANISM: Artificial Sequence
<220> FEATURE:
<223> OTHER INFORMATION: Primer

<400> SEQUENCE: 83
ttcaccaacg ag                                                        12
```

<210> SEQ ID NO 84
<211> LENGTH: 12
<212> TYPE: DNA
<213> ORGANISM: Artificial Sequence
<220> FEATURE:
<223> OTHER INFORMATION: Primer

<400> SEQUENCE: 84
caggtgtggg tt                                                         12

<210> SEQ ID NO 85
<211> LENGTH: 12
<212> TYPE: DNA
<213> ORGANISM: Artificial Sequence
<220> FEATURE:
<223> OTHER INFORMATION: Primer

<400> SEQUENCE: 85
attggtgcag aa                                                         12

<210> SEQ ID NO 86
<211> LENGTH: 12
<212> TYPE: DNA
<213> ORGANISM: Artificial Sequence
<220> FEATURE:
<223> OTHER INFORMATION: Primer

<400> SEQUENCE: 86
aaggcgtgtt ta                                                         12

<210> SEQ ID NO 87
<211> LENGTH: 12
<212> TYPE: DNA
<213> ORGANISM: Artificial Sequence
<220> FEATURE:
<223> OTHER INFORMATION: Primer

<400> SEQUENCE: 87
tattgggatt gg                                                         12

<210> SEQ ID NO 88
<211> LENGTH: 12
<212> TYPE: DNA
<213> ORGANISM: Artificial Sequence
<220> FEATURE:
<223> OTHER INFORMATION: Primer

<400> SEQUENCE: 88
aacatctccg gg                                                         12

<210> SEQ ID NO 89
<211> LENGTH: 12
<212> TYPE: DNA
<213> ORGANISM: Artificial Sequence
<220> FEATURE:
<223> OTHER INFORMATION: Primer

<400> SEQUENCE: 89
atcattggcg aa                                                         12

<210> SEQ ID NO 90
<211> LENGTH: 12
<212> TYPE: DNA
<213> ORGANISM: Artificial Sequence
<220> FEATURE:

<223> OTHER INFORMATION: Primer

<400> SEQUENCE: 90
ttgagtagtt gc                                                               12

<210> SEQ ID NO 91
<211> LENGTH: 12
<212> TYPE: DNA
<213> ORGANISM: Artificial Sequence
<220> FEATURE:
<223> OTHER INFORMATION: Primer

<400> SEQUENCE: 91
tacgccggaa ta                                                               12

<210> SEQ ID NO 92
<211> LENGTH: 12
<212> TYPE: DNA
<213> ORGANISM: Artificial Sequence
<220> FEATURE:
<223> OTHER INFORMATION: Primer

<400> SEQUENCE: 92
cctgaggtag ct                                                               12

<210> SEQ ID NO 93
<211> LENGTH: 12
<212> TYPE: DNA
<213> ORGANISM: Artificial Sequence
<220> FEATURE:
<223> OTHER INFORMATION: Primer

<400> SEQUENCE: 93
gccgcttcag ct                                                               12

<210> SEQ ID NO 94
<211> LENGTH: 12
<212> TYPE: DNA
<213> ORGANISM: Artificial Sequence
<220> FEATURE:
<223> OTHER INFORMATION: Primer

<400> SEQUENCE: 94
atctaaacca cg                                                               12

<210> SEQ ID NO 95
<211> LENGTH: 12
<212> TYPE: DNA
<213> ORGANISM: Artificial Sequence
<220> FEATURE:
<223> OTHER INFORMATION: Primer

<400> SEQUENCE: 95
agagctgaag ta                                                               12

<210> SEQ ID NO 96
<211> LENGTH: 12
<212> TYPE: DNA
<213> ORGANISM: Artificial Sequence
<220> FEATURE:
<223> OTHER INFORMATION: Primer

<400> SEQUENCE: 96
ggtgaggatt ca                                                               12

```
<210> SEQ ID NO 97
<211> LENGTH: 12
<212> TYPE: DNA
<213> ORGANISM: Artificial Sequence
<220> FEATURE:
<223> OTHER INFORMATION: Primer

<400> SEQUENCE: 97
ctcaagcgta ca                                                    12

<210> SEQ ID NO 98
<211> LENGTH: 12
<212> TYPE: DNA
<213> ORGANISM: Artificial Sequence
<220> FEATURE:
<223> OTHER INFORMATION: Primer

<400> SEQUENCE: 98
cctttccgac gt                                                    12

<210> SEQ ID NO 99
<211> LENGTH: 12
<212> TYPE: DNA
<213> ORGANISM: Artificial Sequence
<220> FEATURE:
<223> OTHER INFORMATION: Primer

<400> SEQUENCE: 99
tccttcgagc ag                                                    12

<210> SEQ ID NO 100
<211> LENGTH: 12
<212> TYPE: DNA
<213> ORGANISM: Artificial Sequence
<220> FEATURE:
<223> OTHER INFORMATION: Primer

<400> SEQUENCE: 100
caggccgaag tc                                                    12

<210> SEQ ID NO 101
<211> LENGTH: 12
<212> TYPE: DNA
<213> ORGANISM: Artificial Sequence
<220> FEATURE:
<223> OTHER INFORMATION: Primer

<400> SEQUENCE: 101
aagcctatac ca                                                    12

<210> SEQ ID NO 102
<211> LENGTH: 12
<212> TYPE: DNA
<213> ORGANISM: Artificial Sequence
<220> FEATURE:
<223> OTHER INFORMATION: Primer

<400> SEQUENCE: 102
cgacgatatg at                                                    12

<210> SEQ ID NO 103
<211> LENGTH: 12
<212> TYPE: DNA
<213> ORGANISM: Artificial Sequence
<220> FEATURE:
<223> OTHER INFORMATION: Primer
```

-continued

```
<400> SEQUENCE: 103 gccctttgg ac                                                          12

<210> SEQ ID NO 104
<211> LENGTH: 12
<212> TYPE: DNA
<213> ORGANISM: Artificial Sequence
<220> FEATURE:
<223> OTHER INFORMATION: Primer

<400> SEQUENCE: 104
actttcgatc ca                                                         12

<210> SEQ ID NO 105
<211> LENGTH: 12
<212> TYPE: DNA
<213> ORGANISM: Artificial Sequence
<220> FEATURE:
<223> OTHER INFORMATION: Primer

<400> SEQUENCE: 105
agcactgaat ct                                                         12

<210> SEQ ID NO 106
<211> LENGTH: 12
<212> TYPE: DNA
<213> ORGANISM: Artificial Sequence
<220> FEATURE:
<223> OTHER INFORMATION: Primer

<400> SEQUENCE: 106
gccatcgaaa aa                                                         12

<210> SEQ ID NO 107
<211> LENGTH: 12
<212> TYPE: DNA
<213> ORGANISM: Artificial Sequence
<220> FEATURE:
<223> OTHER INFORMATION: Primer

<400> SEQUENCE: 107
gagtacacga ag                                                         12

<210> SEQ ID NO 108
<211> LENGTH: 12
<212> TYPE: DNA
<213> ORGANISM: Artificial Sequence
<220> FEATURE:
<223> OTHER INFORMATION: Primer

<400> SEQUENCE: 108
cttgagggat gg                                                         12

<210> SEQ ID NO 109
<211> LENGTH: 12
<212> TYPE: DNA
<213> ORGANISM: Artificial Sequence
<220> FEATURE:
<223> OTHER INFORMATION: Primer

<400> SEQUENCE: 109
gcctgcctca cg                                                         12

<210> SEQ ID NO 110
<211> LENGTH: 12
```

<212> TYPE: DNA
<213> ORGANISM: Artificial Sequence
<220> FEATURE:
<223> OTHER INFORMATION: Primer

<400> SEQUENCE: 110
agaggtgtaa at                                                              12

<210> SEQ ID NO 111
<211> LENGTH: 12
<212> TYPE: DNA
<213> ORGANISM: Artificial Sequence
<220> FEATURE:
<223> OTHER INFORMATION: Primer

<400> SEQUENCE: 111
aagctgcagc aa                                                              12

<210> SEQ ID NO 112
<211> LENGTH: 12
<212> TYPE: DNA
<213> ORGANISM: Artificial Sequence
<220> FEATURE:
<223> OTHER INFORMATION: Primer

<400> SEQUENCE: 112
gccttcgtta cg                                                              12

<210> SEQ ID NO 113
<211> LENGTH: 12
<212> TYPE: DNA
<213> ORGANISM: Artificial Sequence
<220> FEATURE:
<223> OTHER INFORMATION: Primer

<400> SEQUENCE: 113
agggctctag gc                                                              12

<210> SEQ ID NO 114
<211> LENGTH: 12
<212> TYPE: DNA
<213> ORGANISM: Artificial Sequence
<220> FEATURE:
<223> OTHER INFORMATION: Primer

<400> SEQUENCE: 114
ttgcataatc gt                                                              12

<210> SEQ ID NO 115
<211> LENGTH: 12
<212> TYPE: DNA
<213> ORGANISM: Artificial Sequence
<220> FEATURE:
<223> OTHER INFORMATION: Primer

<400> SEQUENCE: 115
ggcagatatc at                                                              12

<210> SEQ ID NO 116
<211> LENGTH: 12
<212> TYPE: DNA
<213> ORGANISM: Artificial Sequence
<220> FEATURE:
<223> OTHER INFORMATION: Primer

<400> SEQUENCE: 116

```
tccaagctac ca                                                      12

<210> SEQ ID NO 117
<211> LENGTH: 12
<212> TYPE: DNA
<213> ORGANISM: Artificial Sequence
<220> FEATURE:
<223> OTHER INFORMATION: Primer

<400> SEQUENCE: 117
taacaaccga gc                                                      12

<210> SEQ ID NO 118
<211> LENGTH: 12
<212> TYPE: DNA
<213> ORGANISM: Artificial Sequence
<220> FEATURE:
<223> OTHER INFORMATION: Primer

<400> SEQUENCE: 118
cacaaggaac at                                                      12

<210> SEQ ID NO 119
<211> LENGTH: 12
<212> TYPE: DNA
<213> ORGANISM: Artificial Sequence
<220> FEATURE:
<223> OTHER INFORMATION: Primer

<400> SEQUENCE: 119
tcggtgggaa ta                                                      12

<210> SEQ ID NO 120
<211> LENGTH: 12
<212> TYPE: DNA
<213> ORGANISM: Artificial Sequence
<220> FEATURE:
<223> OTHER INFORMATION: Primer

<400> SEQUENCE: 120
atggagcagg aa                                                      12

<210> SEQ ID NO 121
<211> LENGTH: 12
<212> TYPE: DNA
<213> ORGANISM: Artificial Sequence
<220> FEATURE:
<223> OTHER INFORMATION: Primer

<400> SEQUENCE: 121
ggttcgggaa tg                                                      12

<210> SEQ ID NO 122
<211> LENGTH: 12
<212> TYPE: DNA
<213> ORGANISM: Artificial Sequence
<220> FEATURE:
<223> OTHER INFORMATION: Primer

<400> SEQUENCE: 122
gagctcccga ca                                                      12

<210> SEQ ID NO 123
<211> LENGTH: 12
<212> TYPE: DNA
<213> ORGANISM: Artificial Sequence
```

```
<220> FEATURE:
<223> OTHER INFORMATION: Primer

<400> SEQUENCE: 123
actaacctgg ac                                                               12

<210> SEQ ID NO 124
<211> LENGTH: 12
<212> TYPE: DNA
<213> ORGANISM: Artificial Sequence
<220> FEATURE:
<223> OTHER INFORMATION: Primer

<400> SEQUENCE: 124
ggcgtggttg ta                                                               12

<210> SEQ ID NO 125
<211> LENGTH: 12
<212> TYPE: DNA
<213> ORGANISM: Artificial Sequence
<220> FEATURE:
<223> OTHER INFORMATION: Primer

<400> SEQUENCE: 125
ggcgagggag ga                                                               12

<210> SEQ ID NO 126
<211> LENGTH: 12
<212> TYPE: DNA
<213> ORGANISM: Artificial Sequence
<220> FEATURE:
<223> OTHER INFORMATION: Primer

<400> SEQUENCE: 126
gccgccagag ga                                                               12

<210> SEQ ID NO 127
<211> LENGTH: 12
<212> TYPE: DNA
<213> ORGANISM: Artificial Sequence
<220> FEATURE:
<223> OTHER INFORMATION: Primer

<400> SEQUENCE: 127
tgacacactg tc                                                               12

<210> SEQ ID NO 128
<211> LENGTH: 12
<212> TYPE: DNA
<213> ORGANISM: Artificial Sequence
<220> FEATURE:
<223> OTHER INFORMATION: Primer

<400> SEQUENCE: 128
tgcactacaa ca                                                               12

<210> SEQ ID NO 129
<211> LENGTH: 12
<212> TYPE: DNA
<213> ORGANISM: Artificial Sequence
<220> FEATURE:
<223> OTHER INFORMATION: Primer

<400> SEQUENCE: 129
cacttcaacc ag                                                               12
```

-continued

<210> SEQ ID NO 130
<211> LENGTH: 12
<212> TYPE: DNA
<213> ORGANISM: Artificial Sequence
<220> FEATURE:
<223> OTHER INFORMATION: Primer

<400> SEQUENCE: 130
tatccaccgc tc                                                          12

<210> SEQ ID NO 131
<211> LENGTH: 12
<212> TYPE: DNA
<213> ORGANISM: Artificial Sequence
<220> FEATURE:
<223> OTHER INFORMATION: Primer

<400> SEQUENCE: 131
tgcccactac gg                                                          12

<210> SEQ ID NO 132
<211> LENGTH: 12
<212> TYPE: DNA
<213> ORGANISM: Artificial Sequence
<220> FEATURE:
<223> OTHER INFORMATION: Primer

<400> SEQUENCE: 132
gagactgctg at                                                          12

<210> SEQ ID NO 133
<211> LENGTH: 12
<212> TYPE: DNA
<213> ORGANISM: Artificial Sequence
<220> FEATURE:
<223> OTHER INFORMATION: Primer

<400> SEQUENCE: 133
caggtgggac ca                                                          12

<210> SEQ ID NO 134
<211> LENGTH: 12
<212> TYPE: DNA
<213> ORGANISM: Artificial Sequence
<220> FEATURE:
<223> OTHER INFORMATION: Primer

<400> SEQUENCE: 134
tcctggggcg tt                                                          12

<210> SEQ ID NO 135
<211> LENGTH: 12
<212> TYPE: DNA
<213> ORGANISM: Artificial Sequence
<220> FEATURE:
<223> OTHER INFORMATION: Primer

<400> SEQUENCE: 135
ggcaagggat at                                                          12

<210> SEQ ID NO 136
<211> LENGTH: 12
<212> TYPE: DNA
<213> ORGANISM: Artificial Sequence
<220> FEATURE:
<223> OTHER INFORMATION: Primer

<400> SEQUENCE: 136
gcattgcaat cg                                                    12

<210> SEQ ID NO 137
<211> LENGTH: 12
<212> TYPE: DNA
<213> ORGANISM: Artificial Sequence
<220> FEATURE:
<223> OTHER INFORMATION: Primer

<400> SEQUENCE: 137
gttttgtcac cg                                                    12

<210> SEQ ID NO 138
<211> LENGTH: 12
<212> TYPE: DNA
<213> ORGANISM: Artificial Sequence
<220> FEATURE:
<223> OTHER INFORMATION: Primer

<400> SEQUENCE: 138
ggatccgacg gc                                                    12

<210> SEQ ID NO 139
<211> LENGTH: 12
<212> TYPE: DNA
<213> ORGANISM: Artificial Sequence
<220> FEATURE:
<223> OTHER INFORMATION: Primer

<400> SEQUENCE: 139
atgactgtgc ga                                                    12

<210> SEQ ID NO 140
<211> LENGTH: 12
<212> TYPE: DNA
<213> ORGANISM: Artificial Sequence
<220> FEATURE:
<223> OTHER INFORMATION: Primer

<400> SEQUENCE: 140
gcgtcggttc ga                                                    12

<210> SEQ ID NO 141
<211> LENGTH: 12
<212> TYPE: DNA
<213> ORGANISM: Artificial Sequence
<220> FEATURE:
<223> OTHER INFORMATION: Primer

<400> SEQUENCE: 141
ctcctgctgt tg                                                    12

<210> SEQ ID NO 142
<211> LENGTH: 12
<212> TYPE: DNA
<213> ORGANISM: Artificial Sequence
<220> FEATURE:
<223> OTHER INFORMATION: Primer

<400> SEQUENCE: 142
actgaggggg ga                                                    12

<210> SEQ ID NO 143

```
<211> LENGTH: 12
<212> TYPE: DNA
<213> ORGANISM: Artificial Sequence
<220> FEATURE:
<223> OTHER INFORMATION: Primer

<400> SEQUENCE: 143
aaggacacaa ca                                                          12

<210> SEQ ID NO 144
<211> LENGTH: 12
<212> TYPE: DNA
<213> ORGANISM: Artificial Sequence
<220> FEATURE:
<223> OTHER INFORMATION: Primer

<400> SEQUENCE: 144
acgggtcgta ac                                                          12

<210> SEQ ID NO 145
<211> LENGTH: 12
<212> TYPE: DNA
<213> ORGANISM: Artificial Sequence
<220> FEATURE:
<223> OTHER INFORMATION: Primer

<400> SEQUENCE: 145
gtcggacgtc ca                                                          12

<210> SEQ ID NO 146
<211> LENGTH: 12
<212> TYPE: DNA
<213> ORGANISM: Artificial Sequence
<220> FEATURE:
<223> OTHER INFORMATION: Primer

<400> SEQUENCE: 146
actgagcaac aa                                                          12

<210> SEQ ID NO 147
<211> LENGTH: 12
<212> TYPE: DNA
<213> ORGANISM: Artificial Sequence
<220> FEATURE:
<223> OTHER INFORMATION: Primer

<400> SEQUENCE: 147
cacactcgtc at                                                          12

<210> SEQ ID NO 148
<211> LENGTH: 12
<212> TYPE: DNA
<213> ORGANISM: Artificial Sequence
<220> FEATURE:
<223> OTHER INFORMATION: Primer

<400> SEQUENCE: 148
gtcgccttac ca                                                          12

<210> SEQ ID NO 149
<211> LENGTH: 12
<212> TYPE: DNA
<213> ORGANISM: Artificial Sequence
<220> FEATURE:
<223> OTHER INFORMATION: Primer

<400> SEQUENCE: 149
```
atcgcggaat at                                                              12

<210> SEQ ID NO 150
<211> LENGTH: 12
<212> TYPE: DNA
<213> ORGANISM: Artificial Sequence
<220> FEATURE:
<223> OTHER INFORMATION: Primer

<400> SEQUENCE: 150
agacctgctt ct                                                              12

<210> SEQ ID NO 151
<211> LENGTH: 12
<212> TYPE: DNA
<213> ORGANISM: Artificial Sequence
<220> FEATURE:
<223> OTHER INFORMATION: Primer

<400> SEQUENCE: 151
ttgccgggac ca                                                              12

<210> SEQ ID NO 152
<211> LENGTH: 12
<212> TYPE: DNA
<213> ORGANISM: Artificial Sequence
<220> FEATURE:
<223> OTHER INFORMATION: Primer

<400> SEQUENCE: 152
ggcggttatg aa                                                              12

<210> SEQ ID NO 153
<211> LENGTH: 12
<212> TYPE: DNA
<213> ORGANISM: Artificial Sequence
<220> FEATURE:
<223> OTHER INFORMATION: Primer

<400> SEQUENCE: 153
gtgaccgatc ca                                                              12

<210> SEQ ID NO 154
<211> LENGTH: 12
<212> TYPE: DNA
<213> ORGANISM: Artificial Sequence
<220> FEATURE:
<223> OTHER INFORMATION: Primer

<400> SEQUENCE: 154
gctggcgtat ct                                                              12

<210> SEQ ID NO 155
<211> LENGTH: 12
<212> TYPE: DNA
<213> ORGANISM: Artificial Sequence
<220> FEATURE:
<223> OTHER INFORMATION: Primer

<400> SEQUENCE: 155
ggacctccat cg                                                              12

<210> SEQ ID NO 156
<211> LENGTH: 12
<212> TYPE: DNA

<210> SEQ ID NO 157
<211> LENGTH: 12
<212> TYPE: DNA
<213> ORGANISM: Artificial Sequence
<220> FEATURE:
<223> OTHER INFORMATION: Primer

<400> SEQUENCE: 156
ccgagggctg ta                                                          12

<210> SEQ ID NO 157
<211> LENGTH: 12
<212> TYPE: DNA
<213> ORGANISM: Artificial Sequence
<220> FEATURE:
<223> OTHER INFORMATION: Primer

<400> SEQUENCE: 157
cctgcgggag ga                                                          12

<210> SEQ ID NO 158
<211> LENGTH: 12
<212> TYPE: DNA
<213> ORGANISM: Artificial Sequence
<220> FEATURE:
<223> OTHER INFORMATION: Primer

<400> SEQUENCE: 158
aagtggtggt at                                                          12

<210> SEQ ID NO 159
<211> LENGTH: 12
<212> TYPE: DNA
<213> ORGANISM: Artificial Sequence
<220> FEATURE:
<223> OTHER INFORMATION: Primer

<400> SEQUENCE: 159
tatcctaccg gc                                                          12

<210> SEQ ID NO 160
<211> LENGTH: 12
<212> TYPE: DNA
<213> ORGANISM: Artificial Sequence
<220> FEATURE:
<223> OTHER INFORMATION: Primer

<400> SEQUENCE: 160
aggcaccctt cg                                                          12

<210> SEQ ID NO 161
<211> LENGTH: 12
<212> TYPE: DNA
<213> ORGANISM: Artificial Sequence
<220> FEATURE:
<223> OTHER INFORMATION: Primer

<400> SEQUENCE: 161
gtcgacggac gt                                                          12

<210> SEQ ID NO 162
<211> LENGTH: 12
<212> TYPE: DNA
<213> ORGANISM: Artificial Sequence
<220> FEATURE:
<223> OTHER INFORMATION: Primer

<400> SEQUENCE: 162
gaggagaaac gg                                                          12

<210> SEQ ID NO 163
<211> LENGTH: 12
<212> TYPE: DNA
<213> ORGANISM: Artificial Sequence
<220> FEATURE:
<223> OTHER INFORMATION: Primer

<400> SEQUENCE: 163
gctggattcg ca                                                             12

<210> SEQ ID NO 164
<211> LENGTH: 12
<212> TYPE: DNA
<213> ORGANISM: Artificial Sequence
<220> FEATURE:
<223> OTHER INFORMATION: Primer

<400> SEQUENCE: 164
ggtcaccgat cc                                                             12

<210> SEQ ID NO 165
<211> LENGTH: 12
<212> TYPE: DNA
<213> ORGANISM: Artificial Sequence
<220> FEATURE:
<223> OTHER INFORMATION: Primer

<400> SEQUENCE: 165
atcgcggctt at                                                             12

<210> SEQ ID NO 166
<211> LENGTH: 12
<212> TYPE: DNA
<213> ORGANISM: Artificial Sequence
<220> FEATURE:
<223> OTHER INFORMATION: Primer

<400> SEQUENCE: 166
accatcaaac gg                                                             12

<210> SEQ ID NO 167
<211> LENGTH: 12
<212> TYPE: DNA
<213> ORGANISM: Artificial Sequence
<220> FEATURE:
<223> OTHER INFORMATION: Primer

<400> SEQUENCE: 167
ggccgacttg gc                                                             12

<210> SEQ ID NO 168
<211> LENGTH: 12
<212> TYPE: DNA
<213> ORGANISM: Artificial Sequence
<220> FEATURE:
<223> OTHER INFORMATION: Primer

<400> SEQUENCE: 168
gagtggcaac gt                                                             12

<210> SEQ ID NO 169
<211> LENGTH: 12
<212> TYPE: DNA
<213> ORGANISM: Artificial Sequence
<220> FEATURE:

<223> OTHER INFORMATION: Primer

<400> SEQUENCE: 169
ccgcagggac ca                                                              12

<210> SEQ ID NO 170
<211> LENGTH: 12
<212> TYPE: DNA
<213> ORGANISM: Artificial Sequence
<220> FEATURE:
<223> OTHER INFORMATION: Primer

<400> SEQUENCE: 170
ggtcaggaac aa                                                              12

<210> SEQ ID NO 171
<211> LENGTH: 12
<212> TYPE: DNA
<213> ORGANISM: Artificial Sequence
<220> FEATURE:
<223> OTHER INFORMATION: Primer

<400> SEQUENCE: 171
gtcggtcgtg aa                                                              12

<210> SEQ ID NO 172
<211> LENGTH: 12
<212> TYPE: DNA
<213> ORGANISM: Artificial Sequence
<220> FEATURE:
<223> OTHER INFORMATION: Primer

<400> SEQUENCE: 172
gtgcaatttg gc                                                              12

<210> SEQ ID NO 173
<211> LENGTH: 12
<212> TYPE: DNA
<213> ORGANISM: Artificial Sequence
<220> FEATURE:
<223> OTHER INFORMATION: Primer

<400> SEQUENCE: 173
actcaccacg ca                                                              12

<210> SEQ ID NO 174
<211> LENGTH: 12
<212> TYPE: DNA
<213> ORGANISM: Artificial Sequence
<220> FEATURE:
<223> OTHER INFORMATION: Primer

<400> SEQUENCE: 174
tggcttcatc ac                                                              12

<210> SEQ ID NO 175
<211> LENGTH: 12
<212> TYPE: DNA
<213> ORGANISM: Artificial Sequence
<220> FEATURE:
<223> OTHER INFORMATION: Primer

<400> SEQUENCE: 175
ccgtggaatg ac                                                              12

```
<210> SEQ ID NO 176
<211> LENGTH: 12
<212> TYPE: DNA
<213> ORGANISM: Artificial Sequence
<220> FEATURE:
<223> OTHER INFORMATION: Primer

<400> SEQUENCE: 176
ggaggatggc cc                                                              12

<210> SEQ ID NO 177
<211> LENGTH: 12
<212> TYPE: DNA
<213> ORGANISM: Artificial Sequence
<220> FEATURE:
<223> OTHER INFORMATION: Primer

<400> SEQUENCE: 177
ccttggcatc gg                                                              12

<210> SEQ ID NO 178
<211> LENGTH: 12
<212> TYPE: DNA
<213> ORGANISM: Artificial Sequence
<220> FEATURE:
<223> OTHER INFORMATION: Primer

<400> SEQUENCE: 178
gttagcccca at                                                              12

<210> SEQ ID NO 179
<211> LENGTH: 12
<212> TYPE: DNA
<213> ORGANISM: Artificial Sequence
<220> FEATURE:
<223> OTHER INFORMATION: Primer

<400> SEQUENCE: 179
ggcatggcct tt                                                              12

<210> SEQ ID NO 180
<211> LENGTH: 12
<212> TYPE: DNA
<213> ORGANISM: Artificial Sequence
<220> FEATURE:
<223> OTHER INFORMATION: Primer

<400> SEQUENCE: 180
ggtgacgatg ca                                                              12

<210> SEQ ID NO 181
<211> LENGTH: 12
<212> TYPE: DNA
<213> ORGANISM: Artificial Sequence
<220> FEATURE:
<223> OTHER INFORMATION: Primer

<400> SEQUENCE: 181
actggccggc at                                                              12

<210> SEQ ID NO 182
<211> LENGTH: 12
<212> TYPE: DNA
<213> ORGANISM: Artificial Sequence
<220> FEATURE:
<223> OTHER INFORMATION: Primer
```

```
<400> SEQUENCE: 182
aagctggggg ga                                                            12

<210> SEQ ID NO 183
<211> LENGTH: 12
<212> TYPE: DNA
<213> ORGANISM: Artificial Sequence
<220> FEATURE:
<223> OTHER INFORMATION: Primer

<400> SEQUENCE: 183
atggctactg gc                                                            12

<210> SEQ ID NO 184
<211> LENGTH: 12
<212> TYPE: DNA
<213> ORGANISM: Artificial Sequence
<220> FEATURE:
<223> OTHER INFORMATION: Primer

<400> SEQUENCE: 184
ggtgccggag ca                                                            12

<210> SEQ ID NO 185
<211> LENGTH: 12
<212> TYPE: DNA
<213> ORGANISM: Artificial Sequence
<220> FEATURE:
<223> OTHER INFORMATION: Primer

<400> SEQUENCE: 185
ctcagcgata cg                                                            12

<210> SEQ ID NO 186
<211> LENGTH: 12
<212> TYPE: DNA
<213> ORGANISM: Artificial Sequence
<220> FEATURE:
<223> OTHER INFORMATION: Primer

<400> SEQUENCE: 186
ggtggtggta tc                                                            12

<210> SEQ ID NO 187
<211> LENGTH: 12
<212> TYPE: DNA
<213> ORGANISM: Artificial Sequence
<220> FEATURE:
<223> OTHER INFORMATION: Primer

<400> SEQUENCE: 187
gtcgacgcat ca                                                            12

<210> SEQ ID NO 188
<211> LENGTH: 12
<212> TYPE: DNA
<213> ORGANISM: Artificial Sequence
<220> FEATURE:
<223> OTHER INFORMATION: Primer

<400> SEQUENCE: 188
gacggttcaa gc                                                            12

<210> SEQ ID NO 189
<211> LENGTH: 12
```

```
<212> TYPE: DNA
<213> ORGANISM: Artificial Sequence
<220> FEATURE:
<223> OTHER INFORMATION: Primer

<400> SEQUENCE: 189
aagctgtggg ct                                                          12

<210> SEQ ID NO 190
<211> LENGTH: 12
<212> TYPE: DNA
<213> ORGANISM: Artificial Sequence
<220> FEATURE:
<223> OTHER INFORMATION: Primer

<400> SEQUENCE: 190
gcggaggaac ca                                                          12

<210> SEQ ID NO 191
<211> LENGTH: 12
<212> TYPE: DNA
<213> ORGANISM: Artificial Sequence
<220> FEATURE:
<223> OTHER INFORMATION: Primer

<400> SEQUENCE: 191
ccaggaggtg gt                                                          12

<210> SEQ ID NO 192
<211> LENGTH: 12
<212> TYPE: DNA
<213> ORGANISM: Artificial Sequence
<220> FEATURE:
<223> OTHER INFORMATION: Primer

<400> SEQUENCE: 192
agcgcggcaa aa                                                          12

<210> SEQ ID NO 193
<211> LENGTH: 12
<212> TYPE: DNA
<213> ORGANISM: Artificial Sequence
<220> FEATURE:
<223> OTHER INFORMATION: Primer

<400> SEQUENCE: 193
accactcccg ca                                                          12

<210> SEQ ID NO 194
<211> LENGTH: 12
<212> TYPE: DNA
<213> ORGANISM: Artificial Sequence
<220> FEATURE:
<223> OTHER INFORMATION: Primer

<400> SEQUENCE: 194
ggcggcacag ga                                                          12

<210> SEQ ID NO 195
<211> LENGTH: 12
<212> TYPE: DNA
<213> ORGANISM: Artificial Sequence
<220> FEATURE:
<223> OTHER INFORMATION: Primer

<400> SEQUENCE: 195
```

```
gccccgttag ca                                                    12

<210> SEQ ID NO 196
<211> LENGTH: 12
<212> TYPE: DNA
<213> ORGANISM: Artificial Sequence
<220> FEATURE:
<223> OTHER INFORMATION: Primer

<400> SEQUENCE: 196
aaggcgcgaa cg                                                    12

<210> SEQ ID NO 197
<211> LENGTH: 12
<212> TYPE: DNA
<213> ORGANISM: Artificial Sequence
<220> FEATURE:
<223> OTHER INFORMATION: Primer

<400> SEQUENCE: 197
ggtgactggt gg                                                    12

<210> SEQ ID NO 198
<211> LENGTH: 12
<212> TYPE: DNA
<213> ORGANISM: Artificial Sequence
<220> FEATURE:
<223> OTHER INFORMATION: Primer

<400> SEQUENCE: 198
cgcagccgag at                                                    12

<210> SEQ ID NO 199
<211> LENGTH: 12
<212> TYPE: DNA
<213> ORGANISM: Artificial Sequence
<220> FEATURE:
<223> OTHER INFORMATION: Primer

<400> SEQUENCE: 199
aagaagcagg cg                                                    12

<210> SEQ ID NO 200
<211> LENGTH: 12
<212> TYPE: DNA
<213> ORGANISM: Artificial Sequence
<220> FEATURE:
<223> OTHER INFORMATION: Primer

<400> SEQUENCE: 200
gtgtggaagc ca                                                    12

<210> SEQ ID NO 201
<211> LENGTH: 12
<212> TYPE: DNA
<213> ORGANISM: Artificial Sequence
<220> FEATURE:
<223> OTHER INFORMATION: Primer

<400> SEQUENCE: 201
gatggatttg gg                                                    12

<210> SEQ ID NO 202
<211> LENGTH: 12
<212> TYPE: DNA
<213> ORGANISM: Artificial Sequence
```

```
<220> FEATURE:
<223> OTHER INFORMATION: Primer

<400> SEQUENCE: 202
ggtcaggcac ca                                                              12

<210> SEQ ID NO 203
<211> LENGTH: 12
<212> TYPE: DNA
<213> ORGANISM: Artificial Sequence
<220> FEATURE:
<223> OTHER INFORMATION: Primer

<400> SEQUENCE: 203
tgcctcgcac ca                                                              12

<210> SEQ ID NO 204
<211> LENGTH: 12
<212> TYPE: DNA
<213> ORGANISM: Artificial Sequence
<220> FEATURE:
<223> OTHER INFORMATION: Primer

<400> SEQUENCE: 204
agcagcgcct ca                                                              12

<210> SEQ ID NO 205
<211> LENGTH: 12
<212> TYPE: DNA
<213> ORGANISM: Artificial Sequence
<220> FEATURE:
<223> OTHER INFORMATION: Primer

<400> SEQUENCE: 205
gccagctgta cg                                                              12

<210> SEQ ID NO 206
<211> LENGTH: 12
<212> TYPE: DNA
<213> ORGANISM: Artificial Sequence
<220> FEATURE:
<223> OTHER INFORMATION: Primer

<400> SEQUENCE: 206
ggaggtcgac ca                                                              12

<210> SEQ ID NO 207
<211> LENGTH: 12
<212> TYPE: DNA
<213> ORGANISM: Artificial Sequence
<220> FEATURE:
<223> OTHER INFORMATION: Primer

<400> SEQUENCE: 207
ttcggacgaa ta                                                              12

<210> SEQ ID NO 208
<211> LENGTH: 12
<212> TYPE: DNA
<213> ORGANISM: Artificial Sequence
<220> FEATURE:
<223> OTHER INFORMATION: Primer

<400> SEQUENCE: 208
ggagagcgga cg                                                              12
```

<210> SEQ ID NO 209
<211> LENGTH: 12
<212> TYPE: DNA
<213> ORGANISM: Artificial Sequence
<220> FEATURE:
<223> OTHER INFORMATION: Primer

<400> SEQUENCE: 209
ggcgattctg ca                                                         12

<210> SEQ ID NO 210
<211> LENGTH: 12
<212> TYPE: DNA
<213> ORGANISM: Artificial Sequence
<220> FEATURE:
<223> OTHER INFORMATION: Primer

<400> SEQUENCE: 210
gtgggtggac aa                                                         12

<210> SEQ ID NO 211
<211> LENGTH: 12
<212> TYPE: DNA
<213> ORGANISM: Artificial Sequence
<220> FEATURE:
<223> OTHER INFORMATION: Primer

<400> SEQUENCE: 211
gtgcacgtat gg                                                         12

<210> SEQ ID NO 212
<211> LENGTH: 12
<212> TYPE: DNA
<213> ORGANISM: Artificial Sequence
<220> FEATURE:
<223> OTHER INFORMATION: Primer

<400> SEQUENCE: 212
cgacgacgac ga                                                         12

<210> SEQ ID NO 213
<211> LENGTH: 12
<212> TYPE: DNA
<213> ORGANISM: Artificial Sequence
<220> FEATURE:
<223> OTHER INFORMATION: Primer

<400> SEQUENCE: 213
actggccgag gg                                                         12

<210> SEQ ID NO 214
<211> LENGTH: 12
<212> TYPE: DNA
<213> ORGANISM: Artificial Sequence
<220> FEATURE:
<223> OTHER INFORMATION: Primer

<400> SEQUENCE: 214
gcggtcagca ca                                                         12

<210> SEQ ID NO 215
<211> LENGTH: 12
<212> TYPE: DNA
<213> ORGANISM: Artificial Sequence
<220> FEATURE:
<223> OTHER INFORMATION: Primer -continued

```
<400> SEQUENCE: 215
atcagcgcac ca                                                         12

<210> SEQ ID NO 216
<211> LENGTH: 12
<212> TYPE: DNA
<213> ORGANISM: Artificial Sequence
<220> FEATURE:
<223> OTHER INFORMATION: Primer

<400> SEQUENCE: 216
atggccggtg gg                                                         12
```